United States Patent
Gardner et al.

(10) Patent No.: US 9,216,180 B2
(45) Date of Patent: Dec. 22, 2015

(54) PHARMACEUTICAL COMPOSITIONS AND TREATMENT OF GENETIC DISEASES ASSOCIATED WITH NONSENSE MEDIATED RNA DECAY

(71) Applicants: Lawrence B. Gardner, New York, NY (US); Timothy J. Cardozo, New York, NY (US); Leenus Martin, Harrison, NJ (US)

(72) Inventors: Lawrence B. Gardner, New York, NY (US); Timothy J. Cardozo, New York, NY (US); Leenus Martin, Harrison, NJ (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 14/044,457

(22) Filed: Oct. 2, 2013

(65) Prior Publication Data

US 2014/0094457 A1   Apr. 3, 2014

Related U.S. Application Data

(60) Provisional application No. 61/708,978, filed on Oct. 2, 2012.

(51) Int. Cl.
| | |
|---|---|
| *A61K 31/535* | (2006.01) |
| *A61K 31/415* | (2006.01) |
| *A61K 31/505* | (2006.01) |
| *A61K 31/53* | (2006.01) |
| *A61K 31/4152* | (2006.01) |
| *A61K 45/06* | (2006.01) |
| *G01N 33/50* | (2006.01) |
| *G06F 19/12* | (2011.01) |
| *A61K 31/167* | (2006.01) |
| *A61K 31/34* | (2006.01) |
| *A61K 31/381* | (2006.01) |
| *A61K 31/4035* | (2006.01) |
| *A61K 31/4184* | (2006.01) |
| *A61K 31/4192* | (2006.01) |
| *A61K 31/433* | (2006.01) |
| *A61K 31/445* | (2006.01) |
| *A61K 31/513* | (2006.01) |
| *A61K 31/538* | (2006.01) |
| *G06F 19/16* | (2011.01) |
| *G06F 19/00* | (2011.01) |

(52) U.S. Cl.
CPC ............. *A61K 31/53* (2013.01); *A61K 31/167* (2013.01); *A61K 31/34* (2013.01); *A61K 31/381* (2013.01); *A61K 31/4035* (2013.01); *A61K 31/4152* (2013.01); *A61K 31/4184* (2013.01); *A61K 31/4192* (2013.01); *A61K 31/433* (2013.01); *A61K 31/445* (2013.01); *A61K 31/513* (2013.01); *A61K 31/538* (2013.01); *A61K 45/06* (2013.01); *G01N 33/5023* (2013.01); *G06F 19/12* (2013.01); *G06F 19/16* (2013.01); *G06F 19/706* (2013.01)

(58) Field of Classification Search
CPC ..... A61K 31/4152; A61K 31/53; A61K 45/06; G01N 33/5023; G06F 19/12; G06F 19/16; G06F 19/706
USPC ........... 514/229.5, 230.5, 241, 242, 243, 256, 514/269, 274, 393, 394, 395, 355, 404, 444, 514/471, 535, 616
See application file for complete search history.

(56) References Cited

U.S. PATENT DOCUMENTS

| | | |
|---|---|---|
| 6,372,774 B1 | 4/2002 | Hatton et al. |
| 6,593,344 B1 | 7/2003 | Biedermann et al. |
| 2004/0176372 A1* | 9/2004 | Suto et al. ................. 514/235.5 |
| 2006/0134681 A1 | 6/2006 | Beckmann et al. |
| 2009/0163545 A1* | 6/2009 | Goldfarb ........................ 514/312 |
| 2011/0003843 A1 | 1/2011 | Lejeune et al. |
| 2011/0039911 A1 | 2/2011 | Pe'ery et al. |
| 2012/0046326 A1 | 2/2012 | Aikawa et al. |

FOREIGN PATENT DOCUMENTS

| | | |
|---|---|---|
| WO | 99/18073 A1 | 4/1999 |
| WO | 2005/085189 A2 | 9/2005 |
| WO | 2008/127680 A2 | 10/2008 |
| WO | 2012/012518 A2 | 1/2012 |

OTHER PUBLICATIONS

Lawrence Gardner, "Nonsense Mediated RNA Decay and Cancer: Novel therapeutic Opportunities?" Presentation, Case Western Reserve (Mar. 2, 2012).
Invitation to Pay Additional Fees and, Where Applicable, Protest Fee for PCT Application No. PCT/US13/63064 (Feb. 6, 2014).
International Search Report and Written Opinion for Patent Application No. PCT/US13/63064 (Apr. 14, 2014).
Zhou et al., "Premature Termination Codon Read-Through in the ABCC6 Gene: Potential Treatment for Pseudoxanthoma Elasticum," J. Invest. Dermatol. 133:2672-2677 (2013).
Written Opinion for PCT/US2013/63064 (Apr. 16, 2015).

* cited by examiner

*Primary Examiner* — My-Chau T Tran
(74) *Attorney, Agent, or Firm* — LeClairRyan, a Professional Corporation

(57) ABSTRACT

The present invention relates to pharmaceutical compositions comprising a compound and a pharmaceutically acceptable carrier. The present invention is also directed to a method of treating a genetic disease caused by premature termination codons, or other conditions that render messenger ribonucleic acid (mRNA) susceptible to nonsense mediated RNA decay, in a subject. Also disclosed is a method of inhibiting nonsense mediated RNA decay and/or induction of autophagy. The present invention also relates to a method of identifying inhibitors of nonsense mediated RNA decay and/or inducing autophagy. The present invention further relates to a method of inhibiting nonsense mediated RNA decay and/or induction of autophagy in a subject.

44 Claims, 5 Drawing Sheets

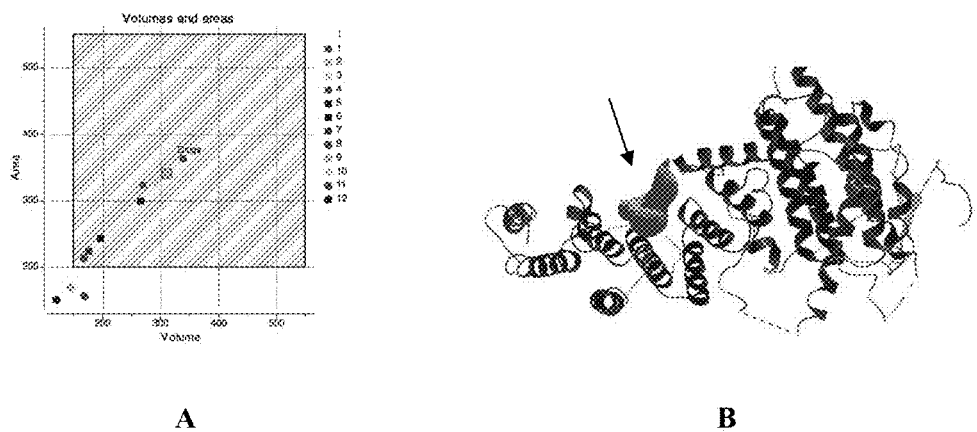
FIGs. 1A-B
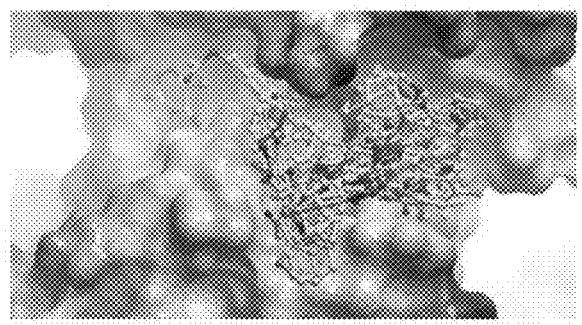
FIG. 2

FIGs. 3A-C

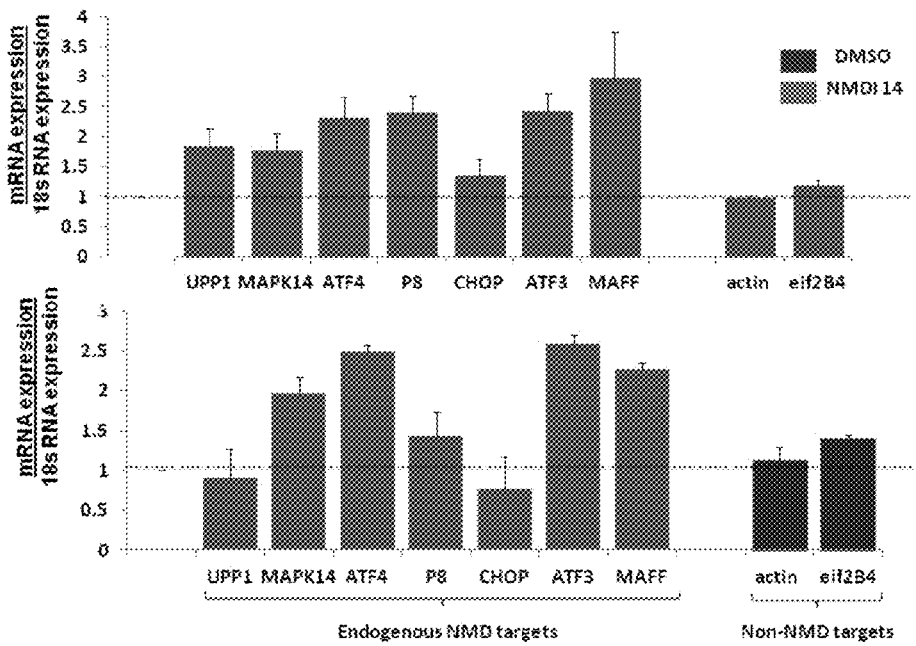
*FIG. 4*
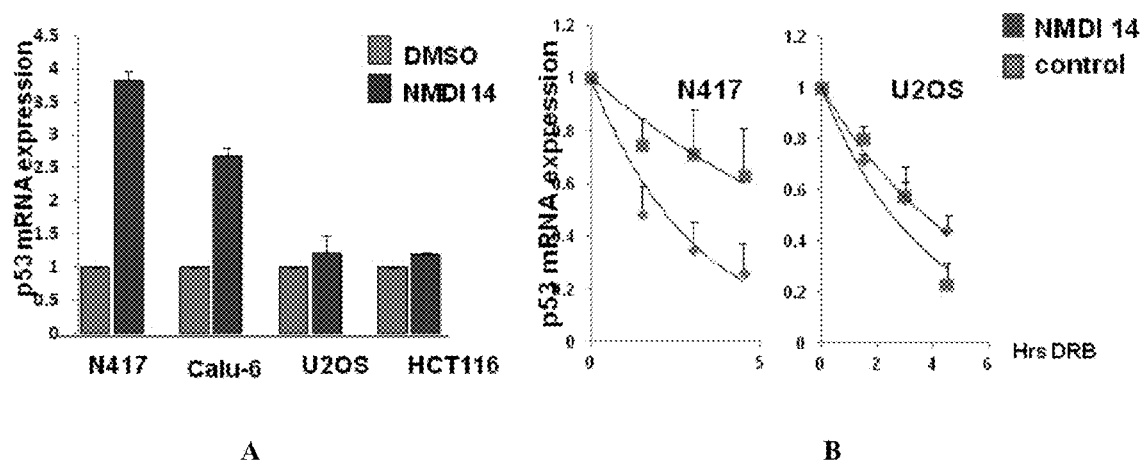
*FIGs. 5A-B*

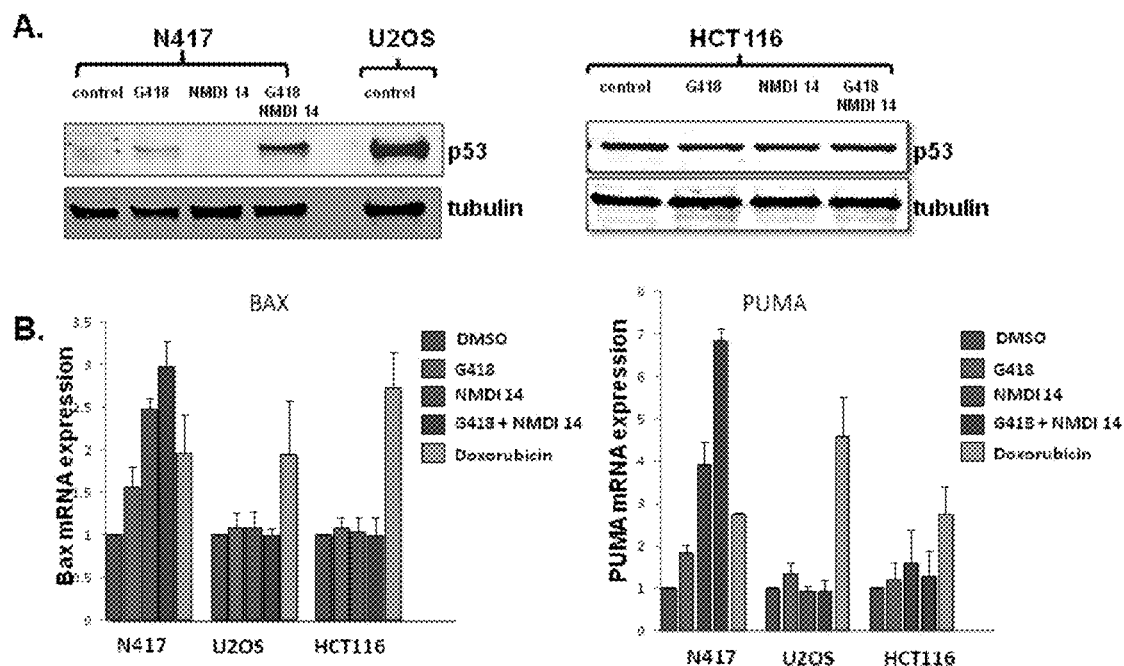
*FIGs. 6A-B*
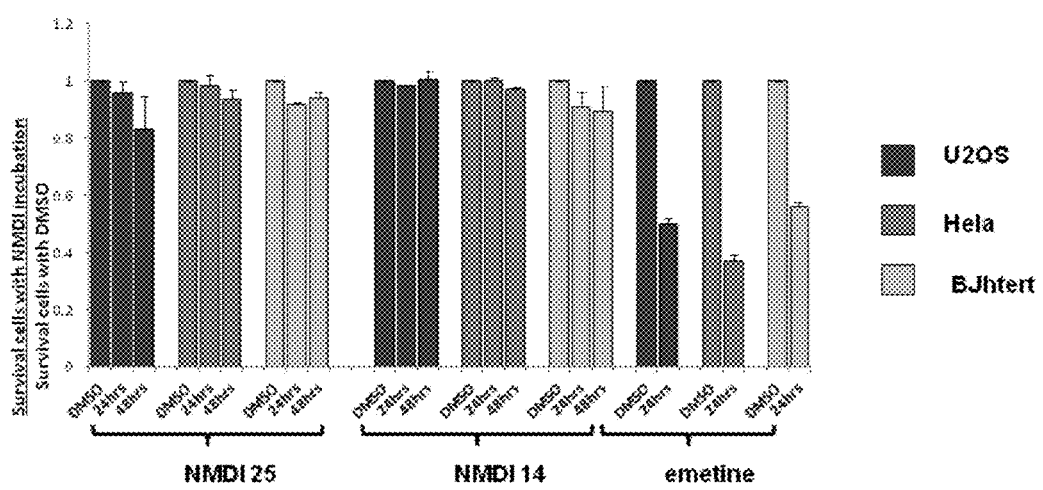
*FIG. 7*

PHARMACEUTICAL COMPOSITIONS AND TREATMENT OF GENETIC DISEASES ASSOCIATED WITH NONSENSE MEDIATED RNA DECAY

This application claims the priority benefit of U.S. Provisional Patent Application Ser. No. 61/708,978, filed Oct. 2, 2012, which is hereby incorporated by reference in its entirety.

FIELD OF THE INVENTION

The present invention is directed to pharmaceutical compositions and treatment of genetic diseases associated with nonsense mediated RNA decay.

BACKGROUND OF THE INVENTION

Genetic disorders are caused by diverse types of mutations. However, many of these mutations, including nonsense mutations, frameshift mutations, and mutations that cause alternative splicing events, result in premature termination codons ("PTC"s). For example, approximately 15% of the mutations in the gene responsible for Duchenne muscular dystophy ("DMD"), a genetic disease that affects one in 3500 males and is characterized by severe, rapid muscle degeneration, are single base changes or multi-exon deletion within exons 44-55 of the DMD gene which result in PTCs (Aartsma-Rus et al., "Entries in the Leiden Duchenne Muscular Dystrophy Mutation Database: An Overview of Mutation Types and Paradoxical Cases that Confirm the Reading-Frame Rule," *Muscle Nerve* 34:135-144 (2006) and Dent et al., "Improved Molecular Diagnosis of Dystrophinopathies in an Unselected Clinical Cohort," *Am. J. Med. Genet. A*. 134:295-298 (2005)). In Sardinia, almost all cases of thalassemia major, a devastating disease characterized by severe anemia, splenomegaly, and iron overload, is caused by a PTC mutation in codon 39 of the β globin gene (Kan et al., "Polymorphism of DNA Sequence in the Beta-Globin Gene Region. Application to Prenatal Diagnosis of Beta 0 Thalassemia in Sardinia," *N. Engl. J. Med*. 302:185-188 (1980) and Maquat et al., "Unstable Beta-Globin mRNA in mRNA-Deficient Beta O Thalassemia," *Cell* 27:543-553 (1981)). In cystic fibrosis ("CF"), a multi-organ disease most marked by pulmonary dysfunction, 10% of the mutations in cystic fibrosis transmembrane conductance regulator ("CFTR") gene worldwide (Bobadilla et al., "Cystic Fibrosis: A Worldwide Analysis of CFTR Mutations—Correlation with Incidence Data and Application to Screening," *Hum. Mutat*. 19:575-606 (2002)), and most of the mutations in Israel (Kerem et al., "Cystic Fibrosis in Jews: Frequency and Mutation Distribution," *Genet. Test*. 1:35-39 (1997)) are nonsense mutations. And 70% of the mutations in enzyme α-L-iduronidase, responsible for Hurler's disease, are PTC mutations (Bunge et al., "Mucopolysaccharidosis Type I: Identification of 8 Novel Mutations and Determination of the Frequency of the Two Common Alpha-L-Iduronidase Mutations (W402X and Q70X) Among European Patients," *Hum. Mol. Genet*. 3:861-866 (1994)). Together, it has been estimated that up to 30% of all mutations resulting in human genetic disorders result in PTCs (Frischmeyer et al., "Nonsense-Mediated mRNA Decay in Health and Disease," *Hum. Mol. Genet*. 8:1893-1900 (1999)). Although screening has reduced the prevalence of these diseases (Kan et al., "Polymorphism of DNA Sequence in the Beta-Globin Gene Region. Application to Prenatal Diagnosis of Beta 0 Thalassemia in Sardinia," *N. Engl. J. Med*. 302:185-188 (1980)) and supportive treatments can improve complications of these disorders, in most cases no direct disease-modifying treatments are available.

Many transcripts carrying a PTC are targeted for rapid degradation before they can be translated into protein through a multistep process termed nonsense mediated RNA decay ("NMD"). During the processing of mammalian pre mRNA, introns are excised and marked by a multi-protein complex termed the exon junction complex ("EJC") (Lykke-Andersen et al., "Communication of the Position of Exon-Exon Junctions to the mRNA Surveillance Machinery by the Protein RNPS1," *Science* 293:1836-1839 (2001); Lykke-Andersen et al., "Human Upf Proteins Target an mRNA for Nonsense-Mediated Decay When Bound Downstream of a Termination Codon," *Cell* 103:1121-1131 (2000); and Modrek et al., "A Genomic View of Alternative Splicing," *Nat. Genet*. 30:13-19 (2002)). When the translation complex pauses at a PTC that is upstream of an EJC, eukaryotic release factors physically bind to and recruit the RNA helicase Upf1, a vital component of the NMD mechanism (Czaplinski et al., "The Surveillance Complex Interacts with the Translation Release Factors to Enhance Termination and Degrade Aberrant mRNAs," *Genes Dev*. 12:1665-1677 (1998); Gehring et al., "Y14 and Hupf3b Form an NMD-Activating Complex," *Mol. Cell* 11:939-949 (2003); Lykke-Andersen et al., "Human Upf Proteins Target an mRNA for Nonsense-Mediated Decay When Bound Downstream of a Termination Codon," *Cell* 103:1121-1131 (2000); and Serin et al., "Identification and Characterization of Human Orthologues to *Saccharomyces cerevisiae* Upf2 Protein and Upf3 Protein (*Caenorhabditis elegans* SMG-4)," *Mol. Cell Biol*. 21:209-223 (2001)). Subsequently, the Upf1 containing complex at the PTC bridges with components in the EJC which promotes the phosphorylation of Upf1. Phosphorylated Upf1 then recruits SMG7, with the subsequent de-phosphorylation of Upf1 by SMG7 (Fukumura et al., "Tumor Microvasculature and Microenvironment: Targets for Anti-Angiogenesis and Normalization," *Microvasc. Res*. 74:72-84 (2007)). The de-phosphorylation of Upf1 by SMG7 is a necessary step in the NMD pathway, prior to the transcript's degradation by exonucleases (Kashima et al., "Binding of a Novel SMG-1-Upf1-Erf1-Erf3 Complex (SURF) to the Exon Junction Complex Triggers Upf1 Phosphorylation and Nonsense-Mediated mRNA Decay," *Genes Dev*. 20:355-367 (2006); Ohnishi et al., "Phosphorylation of hUPF1 Induces Formation of mRNA Surveillance Complexes Containing hSMG-5 and hSMG-7," *Mol. Cell* 12:1187-1200 (2003); and Yamashita et al., "Human SMG-1, a Novel Phosphatidylinositol 3-Kinase-Related Protein Kinase, Associates with Components of the mRNA Surveillance Complex and is Involved in the Regulation of Nonsense-Mediated mRNA Decay," *Genes Dev*. 15:2215-2228 (2001)). Despite insights into the molecular mechanism of NMD, no effective strategy for the pharmacological inhibition of NMD has been developed.

Even a small amount of full length functional protein expressed from the gene containing a PTC may be sufficient to improve the clinical symptoms of a variety of genetic conditions. For example, hemophilia A (which can be marked by PTC mutations) can be effectively treated if the amount of functional factor VIII protein is increased to even 5% of normal (White et al., "Definitions in Hemophilia. Recommendation of the Scientific Subcommittee on Factor VIII and Factor IX of the Scientific and Standardization Committee of the International Society on Thrombosis and Haemostasis," *Thromb. Haemost*. 85:560 (2001)) and 5% of normal CFTR mRNA is sufficient to ameliorate the pulmonary effects in CF (Ramalho et al., "Five Percent of Normal Cystic Fibrosis Transmembrane Conductance Regulator mRNA Ameliorates the Severity of Pulmonary Disease in Cystic Fibrosis," *Am. J. Respir. Cell Mol. Biol.* 27:619-627 (2002)). Unfortunately, the difficulties in effectively and safely achieving these goals with the attractive strategy of gene therapy are well documented. Thus several other strategies have been pursued.

One such approach to treat genetic disorders with PTC mutations is to pharmacologically promote ribosomes to read-through a PTC and produce a full-length protein (Burke et al., "Suppression of a Nonsense Mutation in Mammalian Cells In vivo by the Aminoglycoside Antibiotics G-418 and Paromomycin," *Nuc. Acids Res.* 13:6265-6272 (1985)). For example, treating cells engineered to express a β globin PTC mutated gene with one such agent, the antibiotic gentamicin, leads to real, although small, increases in β☐ globin expression (Salvatori et al., "Production of Beta-Globin and Adult Hemoglobin Following G418 Treatment of Erythroid Precursor Cells from Homozygous Beta(0)39 Thalassemia Patients," *Am. J. Hematol.* 84:720-728 (2009)). Several studies also have shown that gentamicin treatment of cells with PTC mutations of the CFTR can increase cellular chloride transport (Bedwell et al., "Suppression of a CFTR Premature Stop Mutation in a Bronchial Epithelial Cell Line," *Nat. Med.* 3:1280-1284 (1997) and Howard et al., "Aminoglycoside Antibiotics Restore CFTR Function by Overcoming Premature Stop Mutations," *Nat. Med.* 2:467-469 (1996)). In addition, CF patients with PTC mutations treated with intranasal gentamicin increase CFTR protein expression and improve the potential difference of nasal epithelial cells, while no such response was seen in CF patients with non-PTC mutations in the CFTR (Wilschanski et al., "Gentamicin-Induced Correction of CFTR Function in Patients with Cystic Fibrosis and CFTR Stop Mutations," *N. Engl. J. Med.* 349:1433-1441 (2003)).

Because gentamicin is relatively toxic, is inconvenient to administer, and is weak at bypassing PTC mutations (Welch et al., "PTC124 Targets Genetic Disorders Caused by Nonsense Mutations," *Nature* 447:87-91 (2007)), other agents have been developed. A recent high throughput screen identified a small molecule, Ataluren (PTC124/Ataluren) which has similar properties but appears to be more potent and less toxic (Welch et al., "PTC124 Targets Genetic Disorders Caused by Nonsense Mutations," *Nat.* 447:87-91 (2007)) (although the initial screening strategy may have been flawed (Auld et al., "Mechanism of PTC124 Activity in Cell-Based Luciferase Assays of Nonsense Codon Suppression," *Proc. Natl. Acad. Sci. U.S.A.* 106:3585-3590 (2009)). While this drug is being tested in several diseases, including CF, the preclinical use of this drug is most mature in muscular dystrophy. Specifically, Ataluren has been tested in dystrophin knockout mice which transgenetically produce a dystrophin cDNA with a PTC (Welch et al., "PTC124 Targets Genetic Disorders Caused by Nonsense Mutations," *Nat.* 447:87-91 (2007)). Treatment of these mice with Ataluren led to increased expression of full-length dystrophin and an improvement in muscle strength. However, in this model the replacement dystrophin cDNA does not contain introns, and is thus not a NMD target, in contrast to naturally occurring mutations in the dystrophin gene in patients. The bypass of a PTC by Ataluren does not inhibit NMD (Dietz, H. C "New Theraputic Approaches to Mendelian Disorders," *N. Engl. J. Med.* 363:852-863 (2010)), and thus in patients the mutated mRNA is still subjected to NMD. This may be one reason why, although phase II trials in cystic fibrosis and muscular dystrophy have shown promise (e.g., reduction in epithelial electrophysiological abnormalities in CF patients (Kerem et al., "Effectiveness of PTC124 Treatment of Cystic Fibrosis Caused by Nonsense Mutations: A Prospective Phase II Trial," *Lancet.* 372:719-727 (2008)) and improved walk-times in DMD patients (http://ptct.client.shareholder.com/releasedetail.cfm?ReleaseID=518941)), clinical improvements have largely been modest. Thus, alternative or additional treatments may be necessary to make PTC by-pass drugs like Ataluren more effective.

Additional strategies have been employed to compensate for other mutations, which also result in PTCs in various disorders. For example, exon deletions seen in up to 70% of all DMD patients are generally in the rod domain of dystrophin and generate PTCs. Because in-frame deletions of the rod domain result in the clinically milder disease Becker muscular dystrophy, restoration of the reading frame in these DMD patients has been pursued (reviewed in Nelson et al., "Emerging Genetic Therapies to Treat Duchenne Muscular Dystrophy," *Curr. Opin. Neurol.* 22:532-538 (2009)). Strategies such as the use of antisense olignonucleotides to promote exon skipping are being tested in stage I/II studies (reviewed in Nelson et al., "Emerging Genetic Therapies to Treat Duchenne Muscular Dystrophy," *Curr. Opin. Neurol.* 22:532-538 (2009)).

Bypassing PTCs via drugs that either promote PTC read-through, or strategies that promote exon skipping, are likely to be more effective with higher cellular concentrations of PTC mutated mRNA. Indeed, in vitro experiments have demonstrated that the expression of PTC mutated CFTR, as well as CFTR mediated chloride transport, are improved in gentamicin treated cells when Upf1 or Upf2 are also depleted (Linde et al., "Nonsense-Mediated mRNA Decay Affects Nonsense Transcript Levels and Governs Response of Cystic Fibrosis Patients to Gentamicin," *J. Clin. Invest.* 117:683-692 (2007)). Thus, it is hypothesized that the combination of a drug that can bypass a PTC and/or promote exon skipping in combination with a drug that inhibits NMD will reflect a synergistic combination and serve as an effective platform to treat genetic disease. Previously, no pharmacological approach to inhibit NMD has been demonstrated (Welch et al., "PTC124 Targets Genetic Disorders Caused by Nonsense Mutations," *Nat.* 447:87-91 (2007)).

The present invention is directed to overcoming these and other deficiencies in the art.

SUMMARY OF THE INVENTION

One aspect of the present invention relates to a pharmaceutical composition comprising a compound of the formula (I):

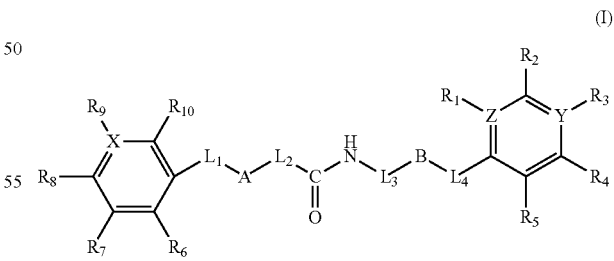

a stereoisomer, pharmaceutically acceptable salt, oxide, solvate, or ester thereof, where
A is selected from the group consisting of:
(1) absent;
(2) —O—;
(3) —CR$_{11}$=CH—;
(4) —S—;
(5) —CHR$_{12}$NH—;

(6) —NR$_{13}$—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
where the substituents of A are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;

B is selected from the group consisting of:
(1) absent;
(2) —O—;
(3) —CR$_{14}$=CH—;
(4) —NH—C(O)—;
(5) —C(S)—NH—;
(6) —N=CH—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
where the substituents of B are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;

L$_1$ to L$_4$ are independently selected from the group consisting of:
(1) absent;
(2) —S$_{0-1}$—C$_{1-6}$ alkylene-S$_{0-1}$—;
(3) —S$_{0-1}$—C$_{2-4}$ alkenylene-S$_{0-1}$—;
(4) —S$_{0-1}$—C$_{2-4}$ alkynylene-S$_{0-1}$—; and
(5) —C(S)—NH—; and
(6) —NH—;

X is C or N;
Z is C, O, or S;
Y is C or absent;
R$_1$ is H, C$_{1-6}$ alkyl, C$_{2-6}$ alkenyl, C$_{2-6}$ alkynyl, OR$_{16}$, C(O)NR$_{17}$R$_{18}$, NR$_{19}$C(O)R$_{20}$;
R$_2$ is H, C$_{1-6}$ alkyl, C$_{2-6}$ alkenyl, C$_{2-6}$ alkynyl, OR$_{16}$, NO$_2$, C(O)N$_{17}$R$_{18}$, NR$_{19}$C(O)R$_{20}$, heterocyclyl or heteroaryl containing 1-5 heteroatoms selected from the group consisting of nitrogen, sulfur, and oxygen;
R$_3$ is H, C$_{1-6}$ alkyl, C$_{2-6}$ alkenyl, C$_{2-6}$ alkynyl, halogen, OR$_{16}$, C(O)NR$_{17}$R$_{18}$, C(O)OR$_{16}$, NR$_{19}$C(O)R$_{20}$;
R$_4$ is H, C$_{1-6}$ alkyl, C$_{2-6}$ alkenyl, C$_{2-6}$ alkynyl, OR$_{16}$, C(O)OR$_{16}$, C(O)NR$_{17}$R$_{18}$, NR$_{19}$C(O)R$_{16}$, heteroaryl containing 1-5 heteroatoms selected from the group consisting of nitrogen, sulfur, and oxygen;
R$_5$ is H, C$_{1-6}$ alkyl, C$_{2-6}$ alkenyl, C$_{2-6}$ alkynyl, halogen, OR$_{16}$, C(O)OR$_{16}$;
R$_6$ is H, C$_{1-6}$ alkyl, C$_{2-6}$ alkenyl, C$_{2-6}$ alkynyl, halogen, OR$_{16}$, NR$_{17}$R$_{18}$, heteroaryl or heterocyclyl containing 1-5 heteroatoms selected from the group consisting of nitrogen, sulfur, and oxygen, N=NR$_{15}$;
R$_7$ is H, C$_{1-6}$ alkyl, C$_{2-6}$ alkenyl, C$_{2-6}$ alkynyl, halogen, OR$_{16}$, NO$_2$, NR$_{19}$C(O)R$_{20}$, S(O)$_2$NR$_{17}$R$_{18}$;
R$_8$ is H, C$_{1-6}$ alkyl, C$_{2-6}$ alkenyl, C$_{2-6}$ alkynyl, halogen, OR$_{16}$, NR$_{19}$C(O)R$_{20}$;
R$_9$ is H, C$_{1-6}$ alkyl, C$_{2-6}$ alkenyl, C$_{2-6}$ alkynyl, halogen, NO$_2$, OR$_{16}$, S(O)$_2$NR$_{21}$R$_{22}$;
R$_{10}$ is H, C$_{1-6}$ alkyl, C$_{2-6}$ alkenyl, C$_{2-6}$ alkynyl, halogen, NR$_{17}$R$_{18}$, OR$_{16}$;

R$_1$ to R$_{10}$ are each optionally substituted 1 to 3 times with substituents selected from the group consisting of halogen, —OH, —OR$_{21}$, —C(O)R$_{21}$, —C(O)OR$_{21}$, C(O)NR$_{21}$R$_{22}$, —NHR$_{21}$, —NR$_{21}$R$_{22}$, —SR$_{21}$, —S(O)R$_{21}$, —S(O)$_2$R$_{21}$, NH$_2$, CN, NO$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;

R$_{11}$ is H, C$_{1-6}$ alkyl, C$_{2-6}$ alkenyl, C$_{3-6}$ alkynyl, NR$_{19}$C(O)R$_{20}$;
R$_{12}$ is H, C$_{1-6}$ alkyl, C$_{2-6}$ alkenyl, C$_{3-6}$ alkynyl, C(O)OR$_{16}$;
R$_{13}$ is NHNH;
R$_{14}$ is C(O)OR$_{21}$;
R$_{10}$ and R$_{12}$ can combine to form a —NH—C(O)— group;
R$_{13}$ and R$_{15}$ can combine to form a —N—N=N— group;
R$_{15}$ to R$_{22}$ are independently H, C$_{1-6}$ alkyl, C$_{2-6}$ alkenyl, C$_{2-6}$ alkynyl, C$_{3-6}$ cycloalkyl, C$_{4-7}$ cycloalkylalky, C$_{1-6}$ alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each R$_{15}$ to R$_{22}$ optionally substituted from 1-3 times with substituents selected from the group consisting of halogen, oxy, OH, CN, NO$_2$, —C(O), NH$_2$, H, C$_{1-6}$ alkyl, C$_{2-6}$ alkenyl, C$_{2-6}$ alkynyl, C$_{3-6}$ cycloalkyl, C$_{4-7}$ cycloalkylalkyl, O-aryl substituted with C$_{1-6}$ alkyl, C(O)NHCH$_2$-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—C$_{1-6}$ alkyl, and a monocyclic aryl;

R$_{21}$ and R$_{22}$ can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, NO$_2$, NH$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, a monocyclic aryl, and monocyclic heteroaryl; and a pharmaceutically acceptable carrier.

Another aspect of the present invention is directed to a pharmaceutical composition comprising a compound of the formula:

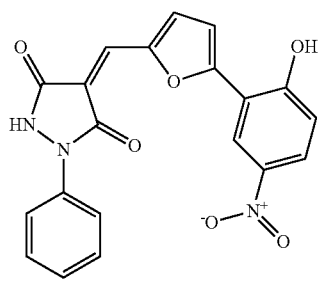

a stereoisomer, pharmaceutically acceptable salt, oxide, solvate, or ester thereof and a pharmaceutically acceptable carrier.

A further aspect of the present invention relates to a pharmaceutical composition comprising a compound of the formula:

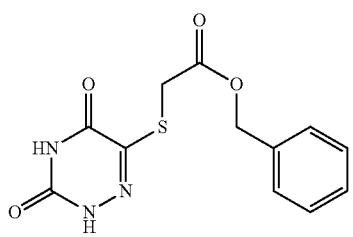 [SMILES: O=C(CSc1n[nH]c(=O)[nH]c1=O)OCc1ccccc1]

a stereoisomer, pharmaceutically acceptable salt, oxide, solvate, or ester thereof and a pharmaceutically acceptable carrier.

Yet another aspect of the present invention is directed to a method of treating a genetic disease caused by premature termination codons, or other conditions that render messenger ribonucleic acid (mRNA) susceptible to nonsense mediated RNA decay, in a subject. This method involves selecting a subject with a genetic disease caused by premature termination codons, or other conditions that render messenger ribonucleic acid (mRNA) susceptible to nonsense mediated RNA decay and administering to the selected subject a compound of the formula

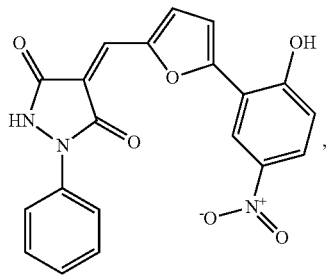

the compound of the formula

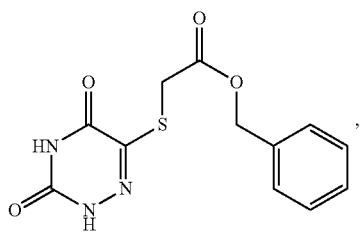 [SMILES: O=C(CSc1n[nH]c(=O)[nH]c1=O)OCc1ccccc1]

or the compound of formula (I):

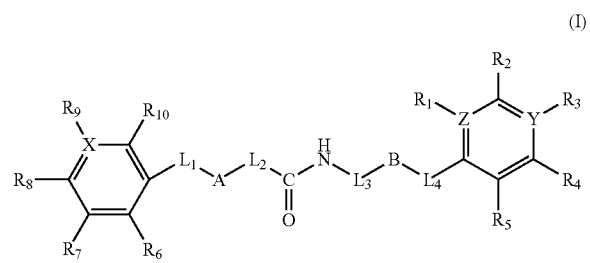

a stereoisomer, pharmaceutically acceptable salt, oxide, solvate, or ester thereof, as defined supra, under conditions effective to treat the genetic disease caused by premature termination codons, or other conditions that render messenger ribonucleic acid (mRNA) susceptible to nonsense mediated RNA decay.

Yet a further aspect of the present invention relates to a method of inhibiting nonsense mediated RNA decay and/or induction of autophagy. This method involves administering to cells a compound of the formula:

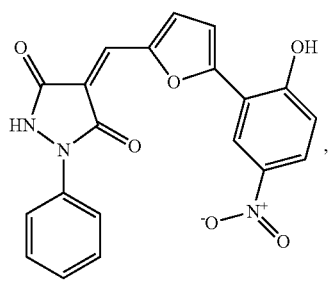

the compound of the formula:

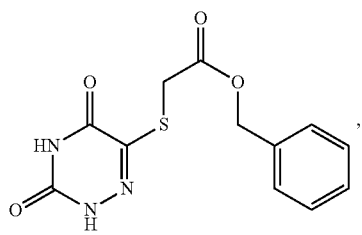 [SMILES: O=C(CSc1n[nH]c(=O)[nH]c1=O)OCc1ccccc1]

or the compound of formula (I):

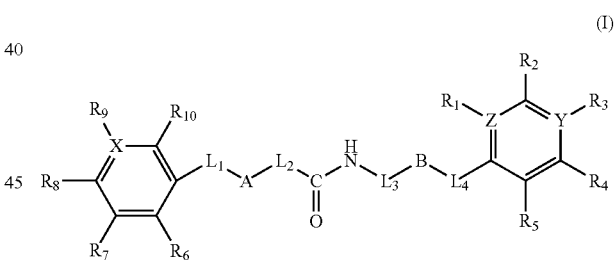

a stereoisomer, pharmaceutically acceptable salt, oxide, solvate, or ester thereof, as defined supra, under conditions effective to inhibit nonsense mediated RNA decay and induce autophagy.

Still another aspect of the present invention relates to a method of identifying inhibitors of nonsense mediated RNA decay and/or inducing autophagy. This method involves providing a model comprising an SMG7-Upf1 complex interface; providing one or more candidate compounds; evaluating contact between the candidate compounds and the model to determine which of the one or more candidate compounds have an ability to bind to and/or fit in the SMG7-Upf1 interface of the first model; and identifying compounds which, based on said evaluating, have the ability to bind to and/or fit in the SMG7-Upf1 interface of the model as compounds potentially useful as inhibitors of nonsense mediated RNA decay and/or inducing autophagy.

Still a further aspect of the present invention relates to a method of inhibiting nonsense mediated RNA decay and/or induction of autophagy in a subject. This method involves selecting a subject in need of inhibiting nonsense mediated RNA decay and/or autophagy; providing a compound which binds to and/or fits in SMG7-Upf1 complex interface; and administering the compound to the selected subject under conditions effective to inhibit nonsense mediated RNA decay and/or to induce autophagy in the subject.

The present invention involves the further development and testing of novel compounds that inhibit NMD. Used in conjunction with validated PTC bypass compounds, NMD inhibition suggests the possibility of pharmacologically generating full length functional protein from patients suffering from a wide variety of screenable genetic diseases.

BRIEF DESCRIPTION OF THE DRAWINGS

FIGS. 1A-B show a plot of SMG7 pocket sizes (FIG. 1A) and an image of the pocket location on SMG7 (FIG. 1B). In FIG. 1A, pockets with volume/area sizes in the hashed square are suitable for drug discovery. The target pocket selected is outlined with a box. In FIG. 1B, the pocket is pointed to by the arrow. SMG7 is depicted in ribbon diagram.

FIG. 2 is a model that shows results of virtual library screening of SMG7, at its interface with Upf1, with >300,000 compounds revealed 31 which are predicted to interrupt Upf1/SMG7 interactions.

In FIG. 3A, wild type and PTC 39 β globin expressing cells were treated with 50 μM NMDIs for 6 h, and RNA was harvested and assessed for β globin expression by quantitative PCR (n=5, with average+SE). Black bars indicate the ratio of PTC to WT expression. In FIG. 3B, cells expressing PTC 39 were treated for 5 h with selected NMDIs and then with DRB to assess stability of the globin mRNA. FIG. 3C shows the results of induction of PTC 39 β globin mRNA after 6 hrs of treatment with various concentrations of selected drugs, ranging from 50 μM to $5 \times 10^{-8}$ μM, normalized to expression with DMSO.

FIG. 4 is a pair of graphs showing that NMDIs stabilize endogenous mRNA. In the upper graph, U2OS and Hela cells were treated with 50 μM of NMDI 14 for 6 hrs, and endogenous non-mutated NMD target expression was assessed. Actin and eIF2Bδ serve as negative controls. In the lower graph, N417 cells, with a PTC mutated p53, were treated with NMDI 14 for 6 hrs and p53 mRNA expression and p53 mRNA stability (C) were assessed.

FIGS. 5A-B show that NMDIs, in combination with G418, increase full length expression of mutated mRNAs. In FIG. 5A, K562 cells expressing either WT or PTC39□β globin were treated with G418 for 72 hrs, NMDI14 for 12 hours, or both, and β globin expression was assessed by immunoblot. In FIG. 5B, N417 cells were treated with either G418 for 24 hrs, NMDI14 for 24 hours, or both, and p53 protein expression was assessed. Full length p53 in U2OS cells is shown as control.

FIGS. 6A-B are pairs of graphs illustrating that combination of read-through drug and NMDI restores full length PTC mutated proteins. In FIG. 6A, cells were treated with DMSO, G418, NMDI, or both for 24 hrs, and full length p53 was assessed in N417 cells or, as a control HCT116 cells. In FIG. 6B, the mRNA expression of the p53 targets Bax (left) and PUMA (right panel) was assessed in N417 cells, U2OS cells, or HCT 116 cells with treatment of DMSO, G418, NMDI, or both.

FIG. 7 is a graph showing that NMDIs are not unduly toxic. U2OS and Hela cells were treated with three NMDIs at 50 μM for 72 hours, and apoptosis was determined by annexin/PI staining Toxicity with translation/NMD inhibitor emetine is shown as control. Average of three readings is shown.

DETAILED DESCRIPTION OF THE INVENTION

Figure 3:
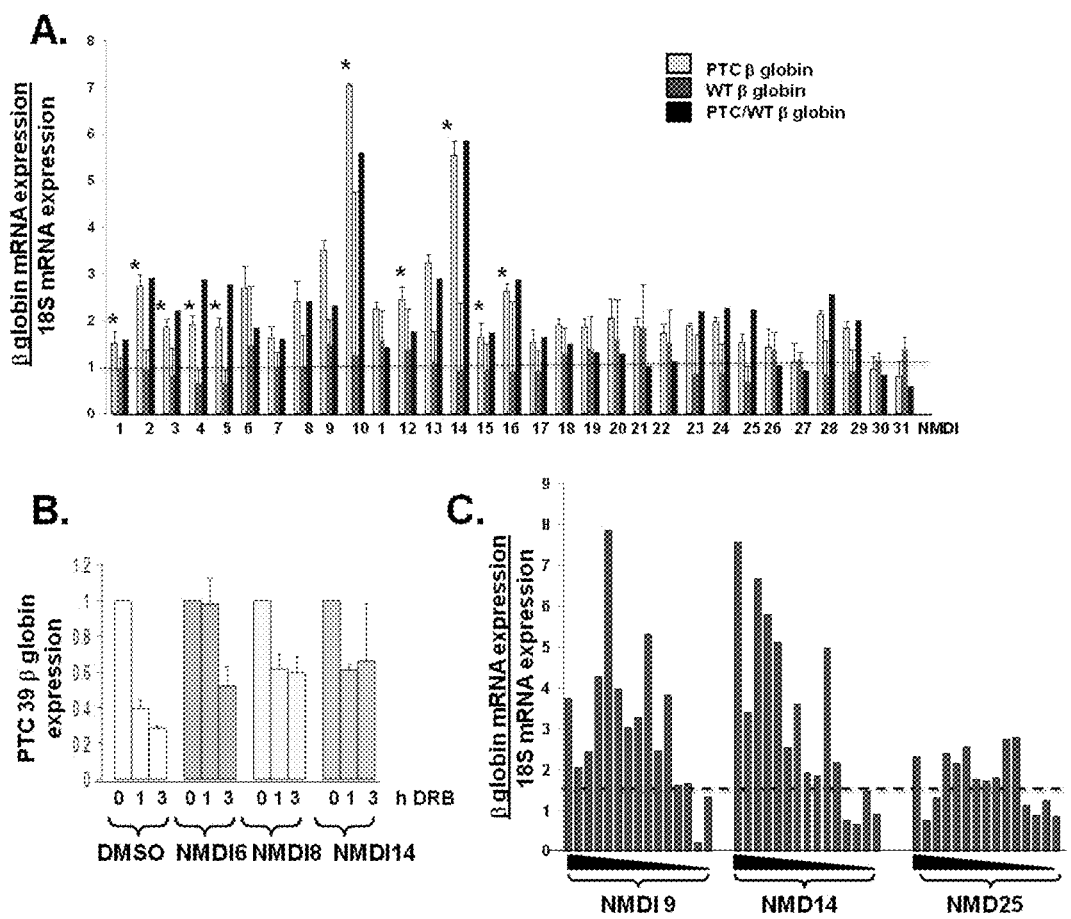
FIGS. 3A-C are graphs demonstrating that NMDIs increase expression and stability of NMD reporters.

One aspect of the present invention relates to a pharmaceutical composition comprising a compound of the formula (I):

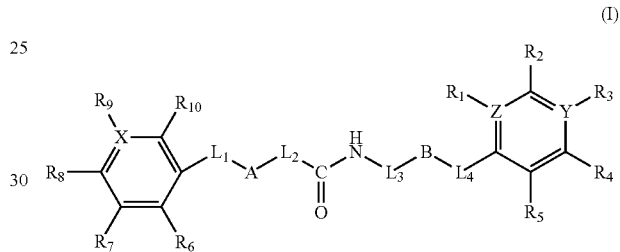

a stereoisomer, pharmaceutically acceptable salt, oxide, solvate, or ester thereof, where
A is selected from the group consisting of:
  (1) absent;
  (2) —O—;
  (3) —CR$_{11}$═CH—;
  (4) —S—;
  (5) —CHR$_{12}$NH—;
  (6) —NR$_{13}$—;
  (7) substituted or unsubstituted C$_{3-8}$ cycloalkylene;
  (8) substituted or unsubstituted arylene;
  (9) substituted or unsubstituted heterocyclylene; and
  (10) substituted or unsubstituted heteroarylene
where the substituents of A are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;
B is selected from the group consisting of:
  (1) absent;
  (2) —O—;
  (3) —CR$_{14}$═CH—;
  (4) —NH—C(O)—;
  (5) —C(S)—NH—;
  (6) —N═CH—;
  (7) substituted or unsubstituted C$_{3-8}$ cycloalkylene;
  (8) substituted or unsubstituted arylene;
  (9) substituted or unsubstituted heterocyclylene; and
  (10) substituted or unsubstituted heteroarylene
where the substituents of B are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;

$L_1$ to $L_4$ are independently selected from the group consisting of:
(1) absent;
(2) —$S_{0-1}$—$C_{1-6}$ alkylene-$S_{0-1}$—;
(3) —$S_{0-1}$—$C_{2-4}$ alkenylene-$S_{0-1}$—;
(4) —$S_{0-1}$—$C_{2-4}$ alkynylene-$S_{0-1}$—; and
(5) —C(S)—NH—; and
(6) —NH—;

X is C or N;
Z is C, O, or S;
Y is C or absent;
$R_1$ is H, $C_{1-6}$ alkyl, $C_{2-6}$ alkenyl, $C_{2-6}$ alkynyl, $OR_{16}$, C(O)$NR_{17}R_{18}$, $NR_{19}C(O)R_{20}$;
$R_2$ is H, $C_{1-6}$ alkyl, $C_{2-6}$ alkenyl, $C_{2-6}$ alkynyl, $OR_{16}$, $NO_2$, C(O)$N_{17}R_{18}$, $NR_{19}C(O)R_{20}$, heterocyclyl or heteroaryl containing 1-5 heteroatoms selected from the group consisting of nitrogen, sulfur, and oxygen;
$R_3$ is H, $C_{1-6}$ alkyl, $C_{2-6}$ alkenyl, $C_{2-6}$ alkynyl, halogen, $OR_{16}$, C(O)$NR_{17}R_{18}$, C(O)$OR_{16}$, $NR_{19}C(O)R_{20}$;
$R_4$ is H, $C_{1-6}$ alkyl, $C_{2-6}$ alkenyl, $C_{2-6}$ alkynyl, $OR_{16}$, C(O)$OR_{16}$, C(O)$NR_{17}R_{18}$, $NR_{19}C(O)R_{16}$, heteroaryl containing 1-5 heteroatoms selected from the group consisting of nitrogen, sulfur, and oxygen;
$R_5$ is H, $C_{1-6}$ alkyl, $C_{2-6}$ alkenyl, $C_{2-6}$ alkynyl, halogen, $OR_{16}$, C(O)$OR_{16}$;
$R_6$ is H, $C_{1-6}$ alkyl, $C_{2-6}$ alkenyl, $C_{2-6}$ alkynyl, halogen, $OR_{16}$, $NR_{17}R_{18}$, heteroaryl or heterocyclyl containing 1-5 heteroatoms selected from the group consisting of nitrogen, sulfur, and oxygen, N=$NR_{15}$;
$R_7$ is H, $C_{1-6}$ alkyl, $C_{2-6}$ alkenyl, $C_{2-6}$ alkynyl, halogen, $OR_{16}$, $NO_2$, $NR_{19}C(O)R_{20}$, $S(O)_2NR_{17}R_{18}$;
$R_8$ is H, $C_{1-6}$ alkyl, $C_{2-6}$ alkenyl, $C_{2-6}$ alkynyl, halogen, $OR_{16}$, $NR_{19}C(O)R_{20}$;
$R_9$ is H, $C_{1-6}$ alkyl, $C_{2-6}$ alkenyl, $C_{2-6}$ alkynyl, halogen, $NO_2$, $OR_{16}$, $S(O)_2NR_{21}R_{22}$;
$R_{10}$ is H, $C_{1-6}$ alkyl, $C_{2-6}$ alkenyl, $C_{2-6}$ alkynyl, halogen, $NR_{17}R_{18}$, $OR_{16}$;
$R_1$ to $R_{10}$ are each optionally substituted 1 to 3 times with substituents selected from the group consisting of halogen, —OH, —$OR_{21}$, —C(O)$R_{21}$, —C(O)$OR_{21}$, C(O)$NR_{21}R_{22}$, —$NHR_{21}$, —$NR_{21}R_{22}$, —$SR_{21}$, —S(O)$R_{21}$, —$S(O)_2R_{21}$, $NH_2$, CN, $NO_2$, $C_{1-6}$ alkyl, $C_{2-6}$ alkenyl, $C_{2-6}$ alkynyl, $C_{3-6}$ cycloalkyl, $C_{4-7}$ cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;
$R_{11}$ is H, $C_{1-6}$ alkyl, $C_{2-6}$ alkenyl, $C_{3-6}$ alkynyl, $NR_{19}C(O)R_{20}$;
$R_{12}$ is H, $C_{1-6}$ alkyl, $C_{2-6}$ alkenyl, $C_{3-6}$ alkynyl, C(O)$OR_{16}$;
$R_{13}$ is NHNH;
$R_{14}$ is C(O)$OR_{21}$;
$R_{10}$ and $R_{12}$ can combine to form a —NH—C(O)— group;
$R_{13}$ and $R_{15}$ can combine to form a —N—N=N— group;
$R_{15}$ to $R_{22}$ are independently H, $C_{1-6}$ alkyl, $C_{2-6}$ alkenyl, $C_{2-6}$ alkynyl, $C_{3-6}$ cycloalkyl, $C_{4-7}$ cycloalkylalky, $C_{1-6}$ alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each $R_{15}$ to $R_{22}$ optionally substituted from 1-3 times with substituents selected from the group consisting of halogen, oxy, OH, CN, $NO_2$, —C(O), $NH_2$, H, $C_{1-6}$ alkyl, $C_{2-6}$ alkenyl, $C_{2-6}$ alkynyl, $C_{3-6}$ cycloalkyl, $C_{4-7}$ cycloalkylalkyl, O-aryl substituted with $C_{1-6}$ alkyl, C(O)$NHCH_2$-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—$C_{1-6}$ alkyl, and a monocyclic aryl;

$R_{21}$ and $R_{22}$ can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, $NO_2$, $NH_2$, $C_{1-6}$ alkyl, $C_{2-6}$ alkenyl, $C_{2-6}$ alkynyl, $C_{3-6}$ cycloalkyl, $C_{4-7}$ cycloalkylalkyl, a monocyclic aryl, and monocyclic heteroaryl; and a pharmaceutically acceptable carrier.

As used herein, the term "halo" or "halogen" means fluoro, chloro, bromo, or iodo.

The term "optionally substituted" indicates that a group may have a substituent at each substitutable atom of the group (including more than one substituent on a single atom), and the identity of each substituent is independent of the others.

The term "substituted" or "substitution" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture, and formulation into an efficacious therapeutic agent. Exemplary substituents include, without limitation, oxo, thio (i.e., =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic heteroaryl, polycyclic aryl, and polycyclic heteroaryl.

The term "monocyclic" indicates a molecular structure having one ring.

The term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain (or the number of carbons designated by "$C_{n-n}$", where n-n is the numerical range of carbon atoms). Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain, or 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butyryl, 3-methylbutynyl, and n-pentynyl.

The term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "heterocyclyl" refers to a stable 3- to 18-membered ring radical which consists of carbon atoms and from one to five heteroatoms selected from the group consisting of nitrogen, oxygen, and sulfur. The heterocyclyl radical may be a monocyclic, or a polycyclic ring system, which may include fused, bridged, or spiro ring systems; and the nitrogen, carbon, or sulfur atoms in the heterocyclyl radical may be optionally oxidized, the nitrogen atom may be optionally quaternized, and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" means an aromatic monocyclic or multi-cyclic ring system of about 5 to about 14 ring atoms, or about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-c]pyrimidinyl, furo[3,2-c]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

Suitable aryl groups for the substituents of the present invention, include, but are not limited to phenyl, naphthyl, azulenyl, fluorenyl, phenanthrenyl, anthracenyl, pyrenyl, triphenylenyl, chrysenyl, and naphthacenyl. Suitable heteroaryl groups of the present invention include, but are not limited to pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl. Exemplary substituted heteroaryl include without limitation pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

Further heterocycles and heteroaryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

The term "alkoxy" means groups of from 1 to 6 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. Alkoxy also includes methylenedioxy and ethylenedioxy in which each oxygen atom is bonded to the atom, chain, or ring from which the methylenedioxy or ethylenedioxy group is pendant so as to form a ring.

The term "carboxy," employed alone or in combination with other terms, refers to a group of the formula —C(=O)OH.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

The term "cycloalkylalkyl" refers to a radical of the formula —$R^aR^b$ where $R^a$ is an alkyl radical as defined above and $R^b$ is a cycloalkyl radical as defined above. The alkyl radical and the cycloalkyl radical may be optionally substituted as defined above.

The term "cycloalkylene" means a group obtained by removal of a hydrogen atom from a cycloalkyl group. Non-limiting examples of cycloalkylene include cyclobutylene and cyclopropylene.

The term "arylene" means a group obtained by removal of a hydrogen atom from an aryl group. Non-limiting examples of arylene include phenylene and naphthylene.

The term "heterocyclylene" means a group obtained by removal of a hydrogen atom from a heterocyclyl group. Non-limiting examples of heterocyclylene include piperidylene, pyrrolidinylene, piperazinylene, morpholinylene, thiomorpholinylene, thiazolidinylene, 1,4-dioxanylene, tetrahydrofuranylene and tetrahydrothiophenylene.

The term "heteroarylene" means a group obtained by removal of a hydrogen atom from a heteroaryl group. Non-limiting examples of heteroarylene include pyridylene, pyrazinylene, furanylene, thienylene and pyrimidinylene.

The term "alkylene" means a group obtained by removal of a hydrogen atom from an alkyl group. Non-limiting examples of alkylene include methylene and ethylene.

The term "alkenylene" means a group obtained by removal of a hydrogen atom from an alkene group.

The term "alkynylene" means a group obtained by removal of a hydrogen atom from an alkyne group.

The present invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The term "compounds of the invention" and equivalent expressions, are meant to embrace compounds herein described, which expression includes the prodrugs, the pharmaceutically acceptable salts, the oxides, and the solvates, e.g. hydrates, where the context so permits.

The term "method of treating" means amelioration or relief from the symptoms and/or effects associated with the disorders described herein.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy,* 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: "Design of Prodrugs," H. Bundgaard, ed., Elsevier (1985); "Methods in Enzymology," K. Widder et al, Ed., Academic Press, 42, p. 309-396 (1985); "A Textbook of Drug Design and Development," Krogsgaard-Larsen and H. Bundgaard, ed., Chapter 5; "Design and Applications of Prodrugs," p. 113-191 (1991); "Advanced Drug Delivery Reviews," H. Bundgard, 8, p. 1-38 (1992); *Journal of Pharmaceutical Sciences*, 77:285 (1988); Nakeya et al, *Chem. Pharm. Bull.,* 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

According to one embodiment, the pharmaceutical composition of the present invention includes a compound of formula (I) where A is a bond, —O—, a $C_{2-6}$ alkenylene with a —$CR_{11}$=CH— moiety, —S—$CH_2$—, —$CH_2CHR_{12}NH$—, —$CH_2NR_{13}$—,

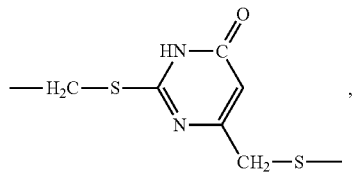

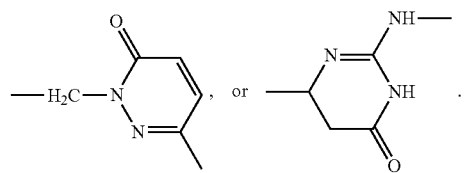

In another embodiment, the pharmaceutical composition of the present invention includes a compound of formula (I) where B is a bond, a $C_{2-6}$ alkenylene with a —$CR_{14}$=CH— moiety, —NH—C(O)—, —C(S)—NH—C($CH_3$)—, —N=CH—,

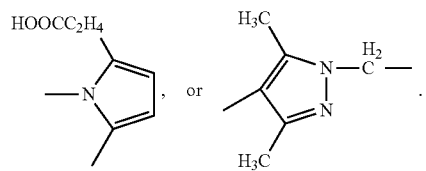

According to another embodiment, the pharmaceutical composition of the present invention includes a compound of formula (I) where A, B, and $L_1$-$L_4$ are absent.

In yet another embodiment, the pharmaceutical composition includes a compound of formula (I) where X is C.

In a further embodiment, the pharmaceutical composition includes a compound of formula (I) where Z is C and Y is C.

In still another embodiment, the pharmaceutical composition includes a compound of formula (I) where X is N.

In a further embodiment, the pharmaceutical composition includes a compound of formula (I) where at least one of $R_1$-$R_{10}$ is independently methyl, halogen, methoxy, or $NO_2$.

In another embodiment, the pharmaceutical composition of the present invention includes a compound selected from

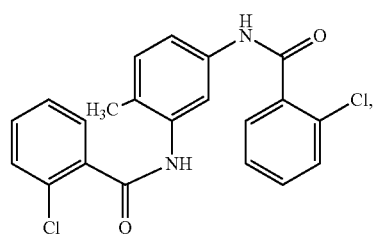

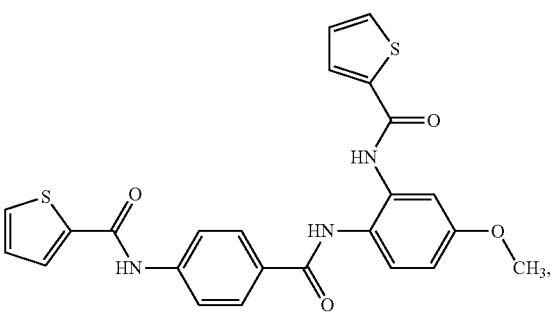

19
-continued
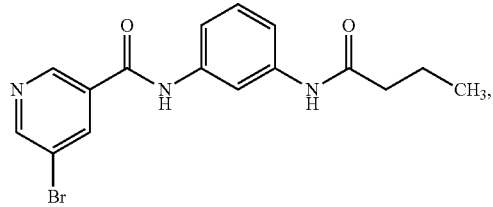
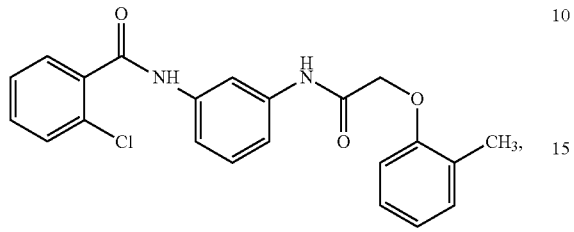
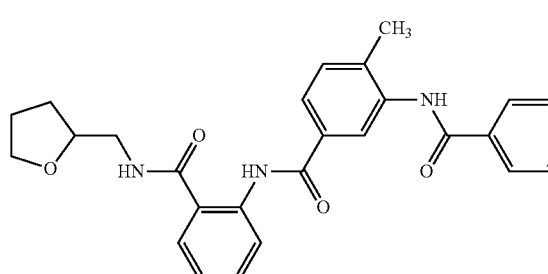
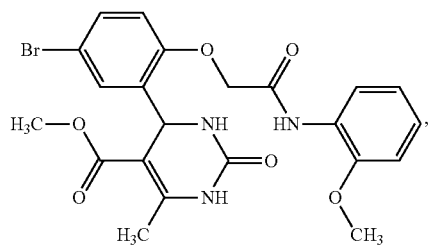
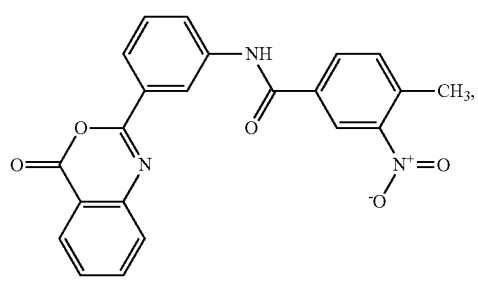
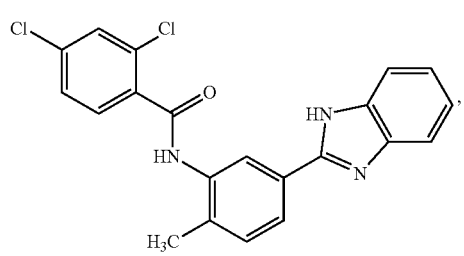
20
-continued
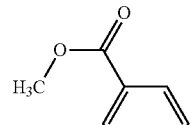
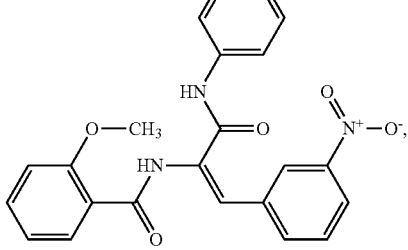
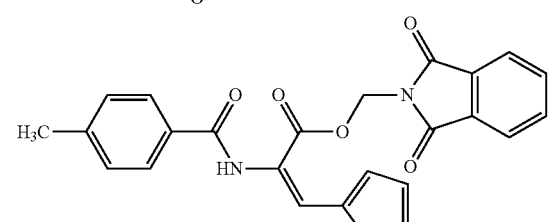
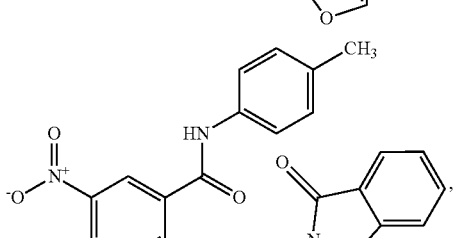
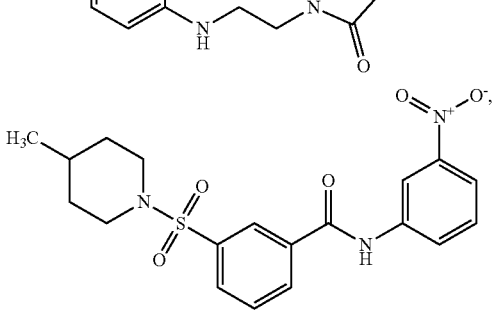
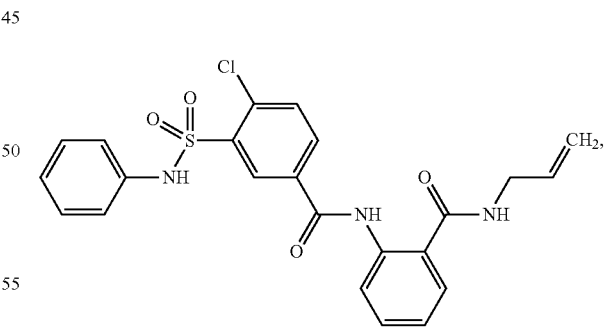
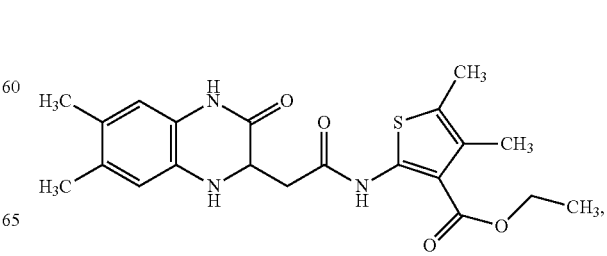

-continued
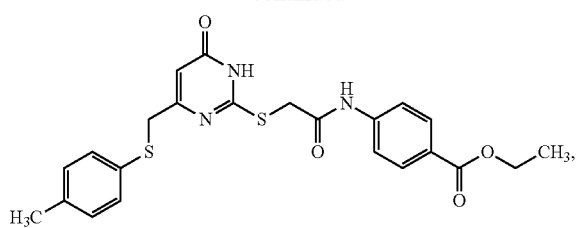
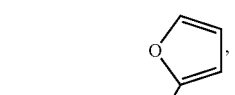
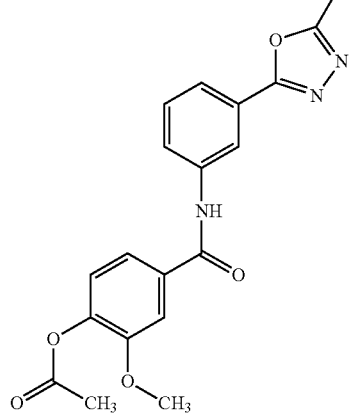
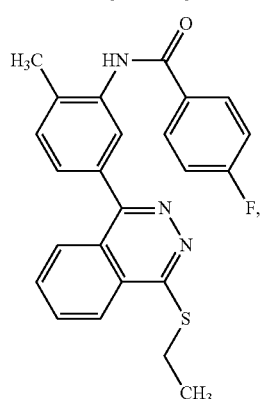
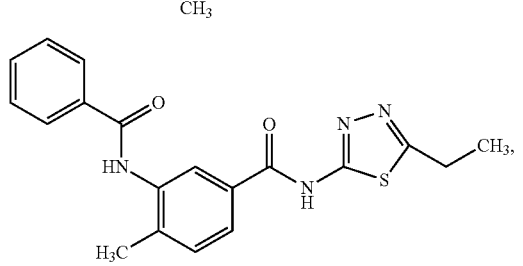
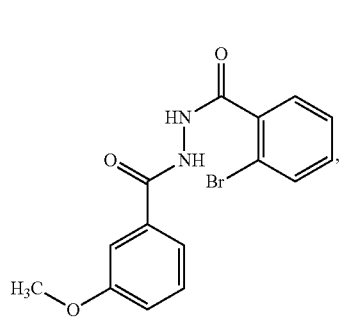
-continued
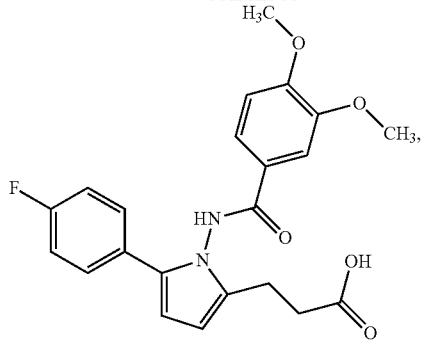
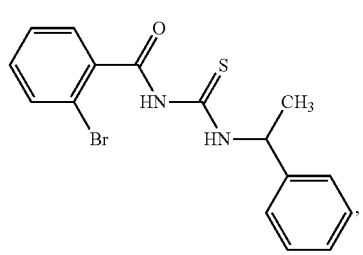
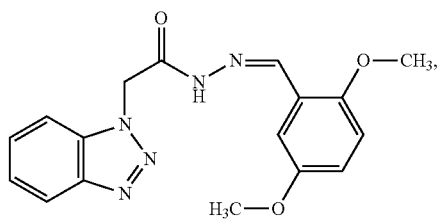
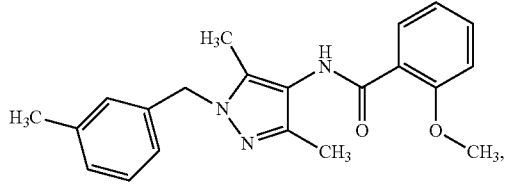
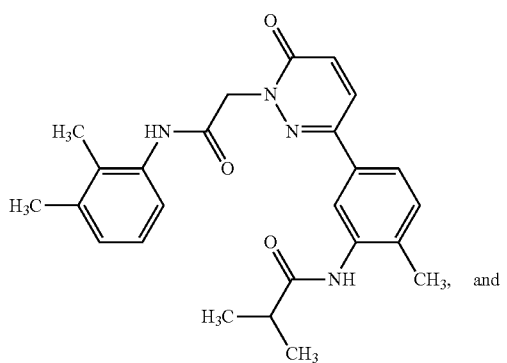
and -continued

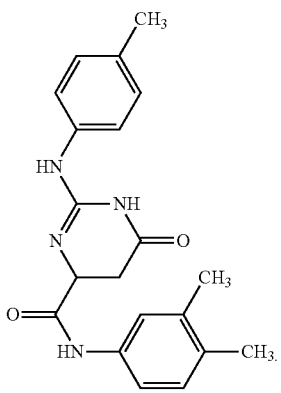

Another aspect of the present invention is directed to a pharmaceutical composition comprising a compound of the formula:

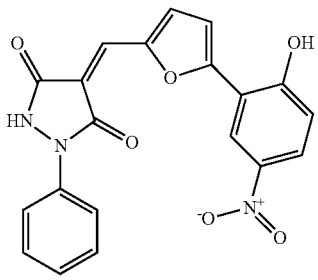

a stereoisomer, pharmaceutically acceptable salt, oxide, solvate, or ester thereof and a pharmaceutically acceptable carrier.

A further aspect of the present invention relates to a pharmaceutical composition comprising a compound of the formula:

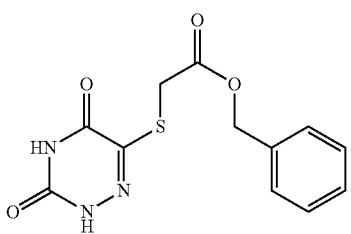 [SMILES: O=C(CSc1n[nH]c(=O)[nH]c1=O)OCc1ccccc1]

a stereoisomer, pharmaceutically acceptable salt, oxide, solvate, or ester thereof and a pharmaceutically acceptable carrier.

The compounds present in the pharmaceutical compositions of the present invention may be obtained from commercial sources, or may be synthesized by methods commonly known to those of ordinary skill in the art. For example, compounds of formula (I) can be prepared by reacting a carboxylic acid of formula (II)

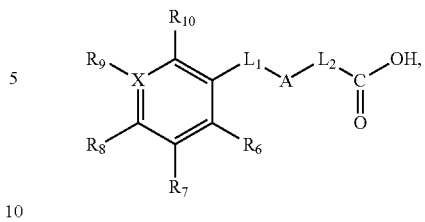

where $R_6$, $R_7$, $R_8$, $R_9$, $R_{10}$, $L_1$, $L_2$, A, and X are as defined herein, or a reactive derivative thereof, with a compound of formula (III)

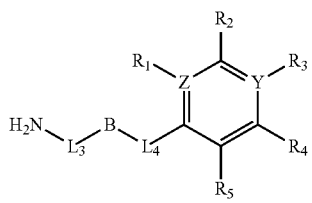

where $R_1$, $R_2$, $R_3$, $R_4$, $R_5$, $L_3$, $L_4$, B, Y, and Z are as defined herein.

Reactive derivatives of the carboxylic acid compounds of formula (II) can be, for example, activated esters, anhydrides, acyl benzotriazoles, acid halides (e.g., acid chlorides) or simple low alkyl esters. Suitable activated esters include, without limitation, p-nitrophenyl ester; 2,4,6-trichlorphenyl ester; pentachlorophenyl ester; cyanomethyl ester; esters of N-hydroxysuccinimide; N-hydroxyphthalimides; 1-hydroxybenzotriazole; N-hydroxypiperidine; 2-hydroxypyridine; or 2-mercaptopyridine.

Reaction of the carboxylic acid compounds of formula (II) with the compounds of formula (III) can also be carried out in the presence of condensation agents such as dicyclohexylcarbodiimide; 1-ethyl-3-(3-dimethylaminpropyl)carbodiimide hydrochloride; and N,N,N',N'-tetramethyl-O-(1H-benzotriazol-1-yl)uronium hexafluorophosphate (HBTU), or others now known or yet to be discovered.

Compounds of formula (III) can be used for reaction as free bases or as acid addition salts, such as inorganic acids (e.g., hydrochlorides or hydrobromides).

Compounds of formula (III) can be mono- or polyamines. If a polyamine, then the use of a suitable nitrogen protecting group may be required, such as a benzyl group, tert-butoxycarbonyl group, Fmoc, or Cbz. Methods describing incorporation and removal of nitrogen protecting groups are known in the art, and are also documented in various monographs, such as Wuts and Greene, "Green's Protective Groups in Organic Synthesis," John Wiley & Sons, 2006 which is hereby incorporated by reference in its entirety.

Reaction of carboxylic acids of formula (II) and their reactive derivatives with compounds of formula (III) may be carried out in a suitable solvent, e.g., an inert solvent. As examples, aromatic hydrocarbons such as benzene, toluene, xylene, halogenated hydrocarbons (e.g., dichloromethane; chloroform; 1,2-dichloroethane; and trichloroethylene), or ethers such as diethyl ether, tetrahydrofuran, dioxane, glycol dimethyl ether, ethyl acetate, acetonitrile, or polar aprotic solvents such as dimethylsulfoxide, dimethylformamide, or N-methylpyrrolidone. Pure solvents, as well as mixtures of two or more, can be used.

The reaction between a carboxylic acid of formula (II) and a compound of formula (III) is optionally carried out in the presence of an auxiliary base. Non-limiting examples of suitable auxiliary bases include alkali metal carbonates such as sodium carbonate or potassium carbonate, alkali metal hydrogen carbonates such as sodium hydrogen carbonate or potassium hydrogen carbonate, or organic bases such as triethylamine, ethyl diisopropylamine, tributylamine, N-methylmorpholine, and pyridine. A suitable excess of the compound of formula (III) can also be used as a base. If compounds of formula (III) are used in the form of their acid addition salts, then it is appropriate to consider the amount of auxiliary base used as an equivalent.

The reaction temperatures can, depending on reactivity of the starting materials, vary widely. Generally, the reaction is carried out at temperatures between −40° C. and 180° C., or between −10° C. and 130° C.

Compounds of formulae (II) and (III) are either known or can be produced according to methods known in the art (see e.g., U.S. Pat. No. 6,593,344 to Biedermann et. al., which is hereby incorporated by reference in its entirety).

In making compounds of formula (I) where B is —C(S)—NH— and $L_3$ is absent, acyl isothiocyanates of formula (IV)

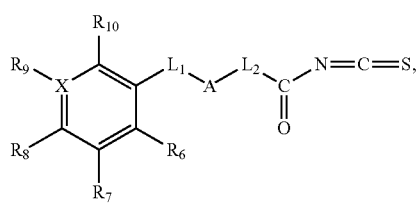

IV where $R_6$, $R_7$, $R_8$, $R_9$, $R_{10}$, $L_1$, $L_2$, A, and X are as defined herein, may be reacted with amines of formula (V)

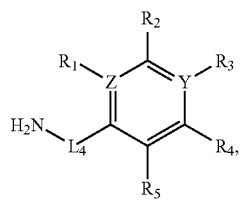

V where $R_1$, $R_2$, $R_3$, $R_4$, $R_5$, $L_4$, Y, and Z are as defined herein (see Parmar et al., "Synthesis and Antibacterial Evaluation of Some Novel 2-Arylamino-4-phenyl-thiazolyl Derivatives," Bull. Korean Chem. Soc. 31(4):793-797 (2010); Pazdera et al., "2-(3-Acylthioureido)benzonitriles. I. Synthesis and Cyclization Reactions of 2-(3-Acylthioureido)benzonitriles," Chem. Papers 45(4):527-540 (1991), which are hereby incorporated by reference in their entirety).

The reaction between formulae (IV) and (V) can be conducted in an organic solvent, e.g., in acetone at room temperature or at the solvent boiling temperature.

Compounds of formula (IV) can be prepared by reacting acyl chlorides of formula (VI)

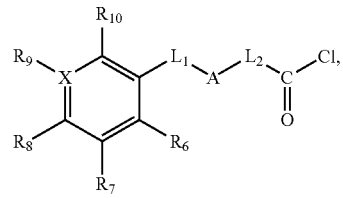

where $R_6$, $R_7$, $R_8$, $R_9$, $R_{10}$, $L_1$, A, and $L_2$ are as defined herein, with potassium thiocyanate or ammonium thiocyanate. The reaction can be conducted, e.g., in acetone at room temperature or at the solvent boiling temperature.

Compounds of formula (VII)

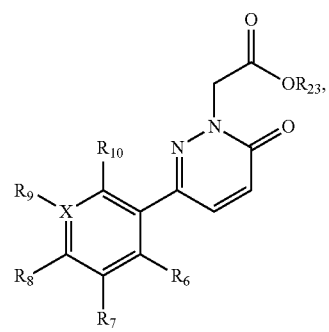

VII where $R_6$, $R_7$, $R_8$, $R_9$, $R_{10}$, X and $OR_{23}$ are as defined herein, which is a low alkyl ester of the compound of formula (II) where A has the following structure:

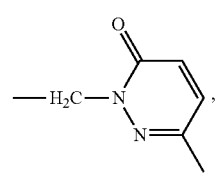

can be prepared by reacting pyridazones of formula (VIII)

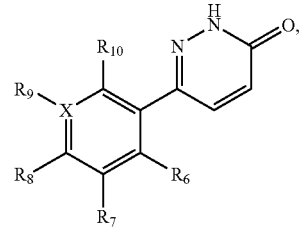

VIII with the following compound: $BrCH_2COOR_{23}$, where $R_{23}$=Me, Et. The reaction can be conducted in N,N-dimethylacetamide (DMAA) in the presence of potassium carbonate at room temperature.

Compounds of formula (VIII) can be prepared by reacting compounds of formula (IX)

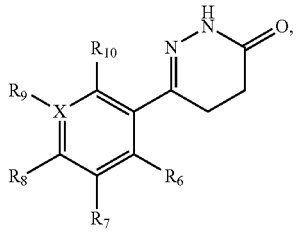

(IX)

where $R_6$, $R_7$, $R_8$, $R_9$, $R_{10}$, and X are as defined herein, with bromine in acetic acid.

Compounds of formula (IX) can be prepared by reacting compounds of formula (X)

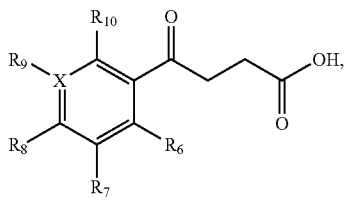

(X)

where $R_6$, $R_7$, $R_8$, $R_9$, $R_{10}$, and X are as defined herein, with hydrazine hydrate.

Compounds of formula (X) can be prepared by reacting compounds of formula (XI)

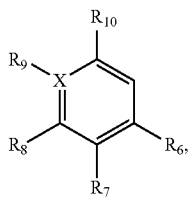

(XI)

where $R_6$, $R_7$, $R_8$, $R_9$, $R_{10}$, and X are as defined herein, with dihydrofuran-2,5-dione.

Compounds of formula (I), where B is —NH—C(O)— and $L_3$ and $L_4$ are absent can be prepared by reacting compounds of formula (XII)

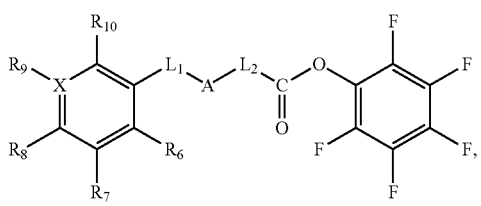

(XII)

where $R_6$, $R_7$, $R_8$, $R_9$, $R_{10}$, $L_1$, $L_2$, A, and X are as defined herein, with compounds of formula (XIII)

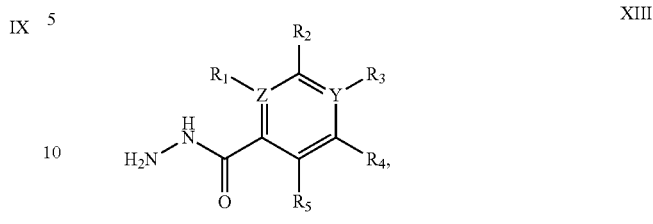

(XIII)

where $R_1$, $R_2$, $R_3$, $R_4$, $R_5$, Y, and Z are as defined herein, in N,N-dimethylformamide at, e.g., 55° C. (see WO 2005/058832 to Finsinger et al, which is hereby incorporated by reference in its entirety).

Compounds of the formula (XII) can be prepared by reacting carboxylic acids of formula (II)

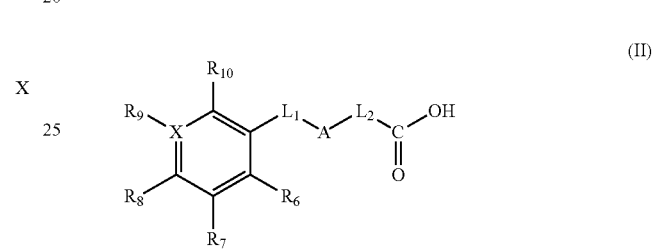

(II)

with pentafluorophenol in the presence of N,N-dicyclohexyl carbodiimide in organic solvent (e.g., 1,4-dioxane) at room temperature.

Compounds of formula (XIII) can be prepared by reacting hydrazine hydrate with the corresponding methyl ester derivative of compound (XIII).

Compounds of formula (I), where $L_3$ is —NH— and B and $L_4$ are absent can be prepared by reacting compounds of formula (XV)

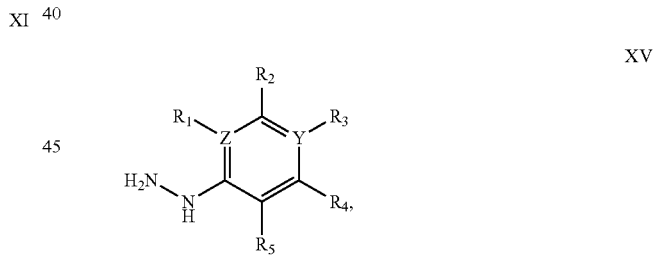

(XV)

where $R_1$, $R_2$, $R_3$, $R_4$, $R_5$, Y, and Z are as defined herein, with compounds of formula (XVI)

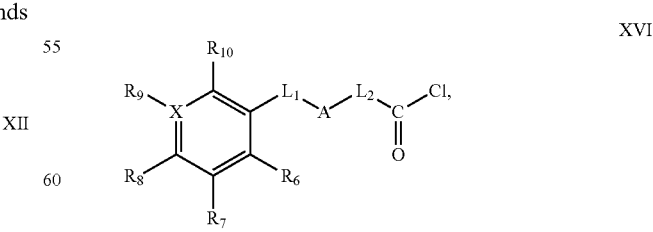

(XVI)

where $R_6$, $R_7$, $R_8$, $R_9$, $R_{10}$, $L_1$, $L_2$, A, and X are as defined herein. The reaction can be carried out in organic solvent or in a mixture of organic solvents, for example, in a 1:1 mixture of dichloromethane and acetonitrile at room temperature (see WO 2008/092861 to Linders et al.; McLeod et al. "Synthetic Applications of Monoprotected Hydrazines toward the Synthesis of 1-Aminopyrroles," *J. Org. Chem.* 61(3):1180-1183 (1996), which are hereby incorporated by reference in their entirety).

Compounds of formula (I), where B is —NH=CH— and L₃ and L₄ are absent can be prepared by reacting compounds of formula (XVII)

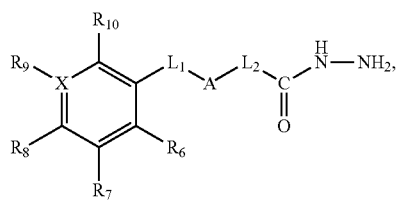

XVII where R₆, R₇, R₈, R₉, R₁₀, L₁, L₂, A, and X are as defined herein, with compounds of formula (XVIII)

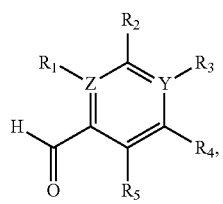

XVIII where R₁, R₂, R₃, R₄, R₅, Y, and Z are as defined herein.

Compounds of formula (XVII) can be prepared by reacting hydrazine hydrate with the corresponding methyl ester derivative of formula (XVII).

The compounds of formula (I) produced according to the described methods can be isolated and purified in a known manner, for example, by subjecting the residue after distillation of the solvent to partition, extraction, re-precipitation, re-crystallization, or another purification method or combination of purification methods. Column chromatography on a suitable support or preparative middle or high pressure liquid chromatography (HPLC) may also be used.

The compound (Z)-4-((5-(2-hydroxy-5-nitrophenyl)furan-2-yl)methylene)-1-phenylpyrazolidine-3,5-dione having the following structure of formula (XIX)

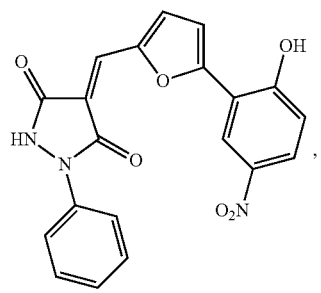

XIX can be prepared by reacting a compound of formula (XX)

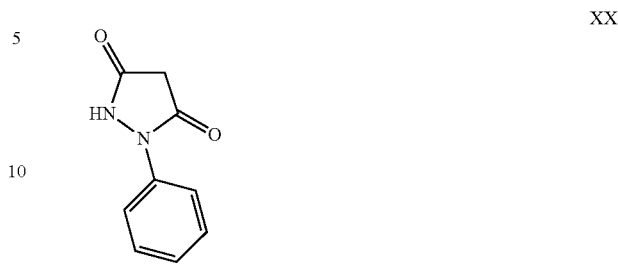

XX with an aldehyde of the formula (XXI)

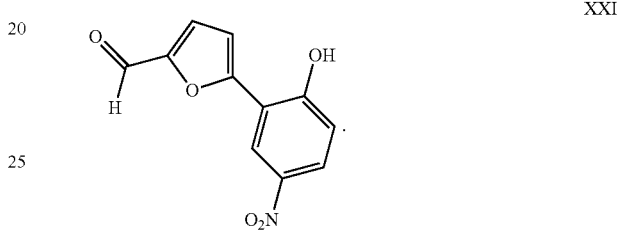

XXI

This reaction can be conducted in acetic acid at the solvent boiling temperature (Liang et al., "Discovering Potent Inhibitors Against c-Met Kinase: Molecular Design, Organic Synthesis and Bioassay," *Org. Biomol. Chem.* 10:421-430 (2012), which is hereby incorporated by reference in its entirety).

Compounds of formula (XX) can be prepared by reacting a compound of formula (XXII)

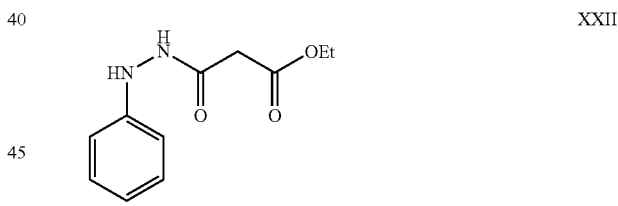

XXII with sodium hydroxide in ethanol at room temperature.

Compounds of formula (XXII) can be prepared by reacting a compound of formula (XXIII)

XXIII with ethyl malonyl chloride in tetrahydrofuran.

The compound 6-((2-Oxo-3-phenoxypropyl)thio)-1,2,4-triazine-3,5(2H,4H)-dione having the structure of formula (XXIV)

can be prepared by reacting a sodium salt of the compound of formula (XXV)

with a compound of formula (XVI)

in ethanol.

Another aspect of the present invention is directed to a method of treating a genetic disease caused by premature termination codons, or other conditions that render messenger ribonucleic acid (mRNA) susceptible to nonsense mediated RNA decay, in a subject. This method involves selecting a subject with a genetic disease caused by premature termination codons, or other conditions that render messenger ribonucleic acid (mRNA) susceptible to nonsense mediated RNA decay and administering to the selected subject a compound of the formula the compound of the formula or the compound of formula (I):

a stereoisomer, pharmaceutically acceptable salt, oxide, solvate, or ester thereof, as defined supra, under conditions effective to treat the genetic disease caused by premature termination codons, or other conditions that render messenger ribonucleic acid (mRNA) susceptible to nonsense mediated RNA decay.

Administering of compounds and/or pharmaceutical compositions to a subject may involve administering therapeutically effective amounts, which means an amount of compound effective in treating the stated conditions and/or disorders in a subject. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

Administering may be carried out orally, intradermally, intramuscularly, intraperitoneally, intravenously, subcutaneously, or intranasally. Compounds may be administered alone or with suitable pharmaceutical carriers, and can be in solid or liquid form, such as tablets, capsules, powders, solutions, suspensions, or emulsions.

Genetic diseases amenable to the treatment method of the present invention include, without limitation, thalassemia, muscular dystrophy, cystic fibrosis, polycystic kidney disease, Hurler's disease, Ullrich disease, spinal muscular atrophy, Fibrillin 1 (FBN1) in Marfan's disease, cancer, cancer with APC mutation, p53 mutation, Wilm's tumor 1 (WT1) mutation, and BRCA 1 and BRCA 2 mutations. Another condition in which the inhibition of NMD might be a part of an effective strategy includes the induction of tumor immunity (see Paston et al., "Induction of Tumor Immunity by Targeted Inhibition of Nonsense-mediated mRNA Decay," Nature 465:227-230 (2010), which is hereby incorporated by reference in its entirety).

In one embodiment, the method of treating a genetic disease caused by premature termination codons, or other conditions that render messenger ribonucleic acid (mRNA) susceptible to nonsense mediated RNA decay, in a subject is carried out in combination with an agent that promotes ribosomal read-through of a premature termination codon to treat the genetic disease or in combination with an agent that inhibits autophagy, such as the antimalarial chloroquine.

A further aspect of the present invention relates to a method of inhibiting nonsense mediated RNA decay and/or induction of autophagy. This method involves administering to cells a compound of the formula:

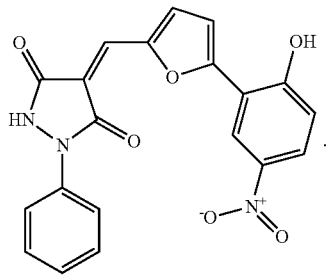

the compound of the formula:

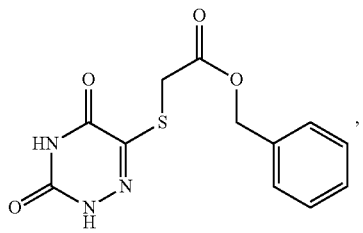 [SMILES: O=C(CSc1n[nH]c(=O)[nH]c1=O)OCc1ccccc1]

or the compound of formula (I):

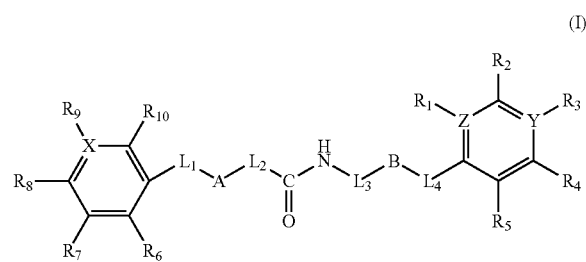

a stereoisomer, pharmaceutically acceptable salt, oxide, solvate, or ester thereof, as defined supra, under conditions effective to inhibit nonsense mediated RNA decay and induce autophagy.

In one embodiment, this method of the present invention is carried out in vitro, such as in a sample. In vitro methods may be carried out to test the activity of certain compounds and/or pharmaceutical compositions against cells in, e.g., a solution or a tissue sample, for their ability to inhibit nonsense mediated RNA decay and/or induction of autophagy.

In another embodiment, this method of the present invention is carried out in vivo in an animal or patient or subject.

Inhibiting nonsense mediated RNA decay and/or induction of autophagy may be accomplished in a cell by any mechanism of action. Without being bound by theory, it is believed that inhibiting nonsense mediated RNA decay and/or induction of autophagy may be achieved by a compound that binds to and/or fits in the SMG7-Upf1 complex interface. Alternatively, inhibiting nonsense mediated RNA decay and/or induction of autophagy in a cell may be achieved by interfering with another step to inhibit NMD, such as through interactions with SMG1.

In one embodiment of this method of the present invention, administering is carried out in combination with an agent that promotes ribosomal read-through of a premature termination codon to treat the genetic disease or in combination with an agent that inhibits autophagy, as discussed supra.

Another aspect of the present invention relates to a method of identifying inhibitors of nonsense mediated RNA decay and/or inducing autophagy. This method involves providing a model comprising an SMG7-Upf1 complex interface; providing one or more candidate compounds; evaluating contact between the candidate compounds and the model to determine which of the one or more candidate compounds have an ability to bind to and/or fit in the SMG7-Upf1 interface of the first model; and identifying compounds which, based on said evaluating, have the ability to bind to and/or fit in the SMG7-Upf1 interface of the model as compounds potentially useful as inhibitors of nonsense mediated RNA decay and/or inducing autophagy.

Providing a model comprising an SMG7-Upf1 complex interface may be carried out by using methods known and used by persons of ordinary skill in the art. In one embodiment, a cell is provided which expresses, e.g., SMG7 and Upf1. To this end, a nucleic acid molecule encoding the desired polypeptide or protein can be introduced into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, e.g. AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others including, but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno sequence about 7-9 bases 5' to the initiation codon (e.g., ATG) to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The protein-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a protein (e.g., SMG7 and/or Upf1) is inserted into a vector in the sense (i.e., 5'→3') direction, such that the open reading frame is properly oriented for the expression of the protein under the control of a promoter of choice. Single or multiple nucleic acids may be ligated into an appropriate vector in this way, under the control of a suitable promoter, to prepare a nucleic acid construct.

Once the isolated nucleic acid molecule encoding the protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

Contact between candidate compounds and a model can be carried out as desired, including, but not limited to, in culture in a suitable growth medium for the cell. Alternatively, mice, rats or other mammals are injected with compounds to be selected.

Methods of identifying inhibitors of nonsense mediated RNA decay and/or inducing autophagy can also be carried out in a cell-free format.

In one embodiment, the assay is directed to the identification of a compound that binds and/or fits in the SMG7-Upf1 interface. This method involves combining SMG7 (or a biologically active portion thereof) and/or Upf1 (or a biologically active portion thereof) in the presence of a test compound under conditions effective to measuring binding and/or interaction of the compound with SMG7 and/or Upf1.

Detection of binding and/or interaction can be achieved through any suitable procedure that is known in the art or hereafter developed. Exemplary procedures for use in a cell-free format include, without limitation, a competitive binding assay, direct measurement, or detecting changes in e.g., the activity of, e.g., SMG7 and/or Upf1.

The assays methods of the present invention can be accomplished in any vessel suitable for containing the reactants. Examples of such vessels include, without limitation, microtiter plates, test tubes, and micro-centrifuge tubes.

In one approach, a fusion protein can be provided which adds a domain that allows one or both of, e.g., SMG7 and Upf1 to be bound to a matrix. For example, SMG7 and Upf1 fusion proteins can be adsorbed onto glutathione sepharose beads (Sigma Chemical; St. Louis, Mo.) or glutathione derivatized microtiter plates, which are then combined with the test compound or the test compound and either the non-adsorbed protein(s), and the mixture incubated under conditions conducive to complex formation (e.g., at physiological conditions for salt and pH). Following incubation, the beads or microtiter plate wells are washed to remove any unbound components, the matrix immobilized in the case of beads, and complex determined either directly or indirectly, for example, as described above. Alternatively, the complexes can be dissociated from the matrix, and the level of protein binding or activity determined using standard techniques.

Other techniques for immobilizing proteins on matrices can also be used in the screening assays of the invention. For example, the protein of interest can be immobilized utilizing conjugation of biotin and streptavidin. Biotinylated protein can be prepared from biotin-NHS(N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with certain proteins (e.g., SMG7 and/or Upf1), but which do not interfere with their binding, can be derivatized to the wells of the plate, and unbound protein trapped in the wells by antibody conjugation. Methods for detecting such complexes, in addition to those described above for the GST-immobilized complexes, include immunodetection of complexes using antibodies reactive with the protein, as well as enzyme-linked assays which rely on detecting an enzymatic activity associated with the protein.

In one embodiment, this method further involves screening the identified compounds in vitro for their ability to inhibit nonsense mediated RNA decay or their ability to induce autophagy or for their ability to treat genetic disease and designating the screened compounds which inhibit nonsense mediated RNA decay or induce autophagy or which treat genetic disease as a useful therapeutic.

In one embodiment, evaluating comprises using automated docking algorithms. Evaluating may involve analyzing electrostatic complementarity, vander Waals interactions, hydrophilic interactions, hydrophobic interactions, and/or hydrogen bonding between the candidate compounds and the first model by methods commonly employed by persons of ordinary skill in the art.

In another embodiment, this method further involves designing de novo compounds based on said identifying. Designing may involve, for example, linking functional groups or small molecule fragments of the identified compounds to form de novo compounds.

A further aspect of the present invention relates to a method of inhibiting nonsense mediated RNA decay and/or induction of autophagy in a subject. This method involves selecting a subject in need of inhibiting nonsense mediated RNA decay and/or autophagy; providing a compound which binds to and/or fits in SMG7-Upf1 complex interface; and administering the compound to the selected subject under conditions effective to inhibit nonsense mediated RNA decay and/or to induce autophagy in the subject.

In one embodiment, administering is carried out in vivo. Administering is carried out as described supra. Suitable subjects include mammals, such as a human.

EXAMPLES

The following examples are provided to illustrate embodiments of the present invention but are by no means intended to limit its scope.

Example 1

Identification and Validation of Pharmacological Nonsense Mediated RNA Decay Inhibitors Results Because translation is necessary for NMD, inhibitors of translation, including emetine and the eIF4AIII binding protein drug pateamine, are effective inhibitors of NMD (Dang et al., "Inhibition of Nonsense-Mediated mRNA Decay by the Natural Product Pateamine A Through Eukaryotic Initiation Factor 4AIII," *J. Biol. Chem.* (2009), which is hereby incorporated by reference in its entirety). Unfortunately, these drugs are not candidates for clinical therapies because (i) as translation is inhibited, the ultimate goal of restoring protein expression is not achieved, and (ii) due to their global inhibition of protein translation these drugs are toxic. As described herein, NMD inhibition can be achieved via other mechanisms. Specifically, phosphorylation of the translation initiation factor eIF2α can be accomplished by a variety of cellular stresses, including hypoxia, ER stress, reactive oxygen species, and the c-myc oncogene, inhibits NMD (Gardner, "Hypoxic Inhibition of Nonsense-Mediated RNA Decay Regulates Gene Expression and the Integrated Stress Response," *Mol. Cell Biol.* 28:3729-3741 (2008); Gardner "Nonsense-Mediated RNA Decay Regulation by Cellular Stress: Implications for Tumorigenesis," *Mol. Cancer Res.* 8:295-308 (2010); and Wang et al., "Inhibition of Nonsense-Mediated RNA Decay by the Tumor Microenvironment Promotes Tumorigenesis," *Mol. Cell Biol.* 31:3670-3680 (2011), which are hereby incorporated by reference in their entirety). Although the inhibition of NMD by these stresses occurs in growing tumors and is necessary for tumorigenesis, the further suppression of NMD by depleting cells of Upf1 with shRNA does not increase tumorigenesis and the molecular manipulation of NMD does not affect the proliferation, or survival of cells (Wang et al., "Inhibition of Nonsense-Mediated RNA Decay by the Tumor Microenvironment Promotes Tumorigenesis," *Mol. Cell Biol.* 31:3670-3680 (2011), which is hereby incorporated by reference in its entirety). These observations suggest that the pharmacological inhibition of NMD can be achieved with limited toxicity or adverse effects, acceptable to DMD, CF, thalassemia, and other genetic disease patients without treatment alternatives.

Identification of Active NMDIs In Silico

Phosphorylation of eIF2α is currently not a viable approach to inhibit NMD in vivo, so other strategies were pursued to develop the concept of nonsense mediated RNA decay inhibitors ("NMDI"s). Because prior studies have demonstrated that NMD activity is dependent on the formation of the Upf1-SMG7 complex, which has been crystallographically resolved (Fukuhara et al., "SMG7 is a 14-3-3-Like Adaptor in the Nonsense-Mediated mRNA Decay Pathway," *Mol. Cell* 17:537-547 (2005), which is hereby incorporated by reference in its entirety), it was determined to take a 3D structure-activity approach to NMDI discovery by targeting the Upf1-SMG7 protein interfaces.

The optimal target pocket on the molecular surface of the 3D structure of SMG7 was identified by a previously published method (Cardozo et al., "Druggability of SCF Ubiquitin Ligase-Protein Interfaces," *Methods Enzymol.* 399:634-653 (2005), which is hereby incorporated by reference in its entirety). Briefly, the crystallographic structure of SMG7 (PDB ID: 1ya0) was analyzed using ICM PocketFinder (Molsoft, LLC, La Jolla, Calif.). Only one pocket was both of suitable size (between 150 and 550 $A^3$) and was lined with functionally sensitive amino acid side chains that mediate the interaction with Upf1 (FIGS. 1A-B). This pocket was selected for virtual library screening ("VLS").

VLS rapidly docks flexible chemical ligands to a grid representation of the receptor 3D structure followed by an evaluation of the docked conformation with a scoring function. ICM-VLS (Molsoft, LLC, La Jolla, Calif.) was used. ICM uses a full atom representation of the chemical ligand. The ICM scoring function integrates van der Waals energy, electrostatics, hydrogen bonding, conformational entropy loss and solvation electrostatic energy change (Abagyan et al., "Biased Probability Monte Carlo Conformational Searches and Electrostatic Calculations for Peptides and Proteins," *J. Mol. Biol.* 235:983-1002 (1994), which is hereby incorporated by reference in its entirety). The algorithms have been previously validated by the successful identification of novel antagonists of the proteins in several distinct families, such as thyroid hormone receptor (Schapira et al., "Discovery of Diverse Thyroid Hormone Receptor Antagonists by High-Throughput Docking," *Proc. Natl. Acad. Sci. U.S.A.* 100: 7354-7359 (2003), which is hereby incorporated by reference in its entirety) and adenosine A2A receptor (Katritch et al., "Structure-Based Discovery of Novel Chemotypes for Adenosine A(2A) Receptor Antagonists," *J. Med. Chem.* 53:1799-1809 (2010), which is hereby incorporated by reference in its entirety), and histone acetyltransferase (Bowers et al., "Virtual Ligand Screening of the P300/CBP Histone Acetyltransferase: Identification of a Selective Small Molecule Inhibitor," *Chem. Biol.* 17:471-482 (2010), which is hereby incorporated by reference in its entirety). These cases are not significantly different in structural quality or scope from the SMG7 study carried out here.

Analysis of the protein interfaces of SMG7 revealed a "druggable" pocket of suitable size and location to, in principle, disrupt the interaction of Upf1 with SMG7. This site exhibited additional features predictive of successful inhibitor discovery: (a) critical amino acid interactions between the two proteins have been determined, and some line the identified pocket; (b) the interaction of Up1/SMG7 has been found to be necessary for NMD; (c) though Upf1 and SMG7 may have additional non-NMD roles, the interaction between the two appears to be unique for NMD. To identify SMG7-Upf1 inhibitors, the selected pocket site was screened against a collection of 315,102 compounds of the ChemBridge Express Library (San Diego, Calif., USA) using default ICM-docking parameters on three 3.0-GHz Intel Xeon processors. The resulting compounds achieving a docking score of <32 were further filtered by selecting those with extensive hydrogen bonds and van der Waals contacts, followed by hierarchical clustering for a diversity of scaffolds. The 31 most diverse compounds chosen from different clusters were then selected for in vitro testing (FIG. 2).

To test these putative NMDIs, a common and straightforward assay for NMD was utilized which uses fibroblasts stably expressing constructs for either wild-type β globin or a β globin with a PTC. This PTC 39 β globin mutation is responsible for greater than 90% of thalassemia major in areas of the Mediterranean, and is well established to be degraded rapidly by NMD (Chang et al., "Beta 0 Thalassemia, A Nonsense Mutation in Man," *Proc. Natl. Acad. Sci. U.S.A.* 76:2886-2889 (1979), which is hereby incorporated by reference in its entirety). For example, when new transcription is inhibited with the addition of the RNA polymerase II inhibitor DRB, the stability of the PTC 39 β globin mRNA is diminished compared to the stability of the wild-type β☐ globin construct (Gardner, "Hypoxic Inhibition of Nonsense-Mediated RNA Decay Regulates Gene Expression and the Integrated Stress Response," *Mol. Cell Biol.* 28:3729-3741 (2008), which is hereby incorporated by reference in its entirety). In addition, knock-down of Upf1 or inhibition of NMD with the translation inhibitor emetine selectively stabilizes the PTC39 construct while not affecting the wild-type globin construct (Gardner, "Hypoxic Inhibition of Nonsense-Mediated RNA Decay Regulates Gene Expression and the Integrated Stress Response," *Mol. Cell Biol.* 28:3729-3741 (2008), which is hereby incorporated by reference in its entirety).

To determine if the putative NMDIs actually inhibit NMD, cells expressing either the wild-type or PTC 39 β☐ globin genomic constructs were first treated with 50 μM of the 31 identified compounds for 6 hours. RNA was then harvested and expression of PTC β globin and wild-type ☐β globin was determined using real time PCR. Roughly ten compounds were identified that selectively increased the expression level of PTC 39☐β globin greater than 2-fold, without affecting wild-type β globin expression, with a p value<0.05 (FIG. 3A).

These compounds were then used in a secondary screen to examine stability of transcripts in their presence. Briefly, cells expressing either wild-type of PTC 39□β globin were treated with compound for 6 hours, and the DRB was added. RNA was collected at time 0, 1.5, and 3 hrs after DRB addition, and expression of globin was assessed by real time PCR. In two separate cell lines (U2OS osteosarcoma cell lines and mouse embryo fibroblast cells), it was found that NMDIs stabilized the NMD-degraded transcript without interfering with the wild-type transcript (FIG. 3B).

Identified NMDIs are Effective at Low Concentrations

All compounds that showed activity at 50 µM, 5 µM, and 0.5 µM were tested. While some compounds showed decreased effectiveness at lower concentrations, others showed more activity at lower concentrations as has been noted with other small molecule inhibitors. Remarkably, further testing revealed that several of these NMDIs were active at nanomolar concentrations (FIG. 3C).

Identified NMDIs Also Increase the Expression of Endogenous NMD Targets

While NMD has been primarily appreciated as a mechanism to rapidly degrade mutated transcripts, it was been demonstrated that a wide variety of non-mutated transcripts are also degraded by NMD (Gardner, "Hypoxic Inhibition of Nonsense-Mediated RNA Decay Regulates Gene Expression and the Integrated Stress Response," *Mol. Cell Biol.* 28:3729-3741 (2008); Mendell et al., "Nonsense Surveillance Regulates Expression of Diverse Classes of Mammalian Transcripts and Mutes Genomic Noise," *Nat. Genet.* 36:1073-1078 (2004); and Wang et al., "Inhibition of Nonsense-Mediated RNA Decay by the Tumor Microenvironment Promotes Tumorigenesis," *Mol. Cell Biol.* 31:3670-3680 (2011), which are hereby incorporated by reference in their entirety). Most recently, a non-biased assessment of global mRNA stability has been performed under a variety of conditions that inhibit NMD, and over 700 transcripts that are degraded by NMD have been identified (Wang et al., "Inhibition of Nonsense-Mediated RNA Decay by the Tumor Microenvironment Promotes Tumorigenesis," *Mol. Cell Biol.* 31:3670-3680 (2011), which is hereby incorporated by reference in its entirety). Many of these targets play an important role in stress response. For example, it has been reported that many components of the integrated stress response are targeted by NMD, including ATF-4, ATF-3, and CHOP. The upregulation of these targets with the molecular inhibition of NDM leads to improved stress response, an important response in many diseases including diabetes. In preliminary experiments assessing the steady state mRNA expression of seven non-mutated NMD targets by real-time PCR, it was noted that all these mRNAs increased in U2OS and/or Hela cells after treatment with NMDIs (FIG. 4).

NMDIs Increase the Stability and Expression of an Endogenous Mutated mRNA

Preliminary data suggest that NMDIs can increase the stability and expression of both reporter constructs of a PTC mutant (FIGS. 3A-C) and endogenous NMD targets (FIG. 4). It was next determined whether the NMDIs can work on mutated endogenously expressed mRNAs. The small cell lung cancer cell line N417 has a p53 tumor suppressor gene that is deleted on one allele and carries a PTC mutation (GAG to TAG in exon 298) on the other allele that renders it a target for NMD. When treated with an NMDI, increased expression and stability of the mutated p53 mRNA was observed (FIG. 4). Similar effects were seen in the Calu-6 cancer cell line, whose p53 gene also contains a PTC mutation. No such effect was seen in cells expressing wild-type p53 in two other cell lines (FIG. 4).

NMDI, Along with a PTC "Read-Through" Drug, Increases the Protein Expression of a NMD Reporter and Endogenous NMD Targets While several NMDIs increase the stability and expression of NMD targeted mRNAs, a clinically effective strategy demands the expression of a full length, biologically active protein. As noted previously, there are several drugs that can promote read-through of PTCs. The most effective agent at non-toxic concentrations, Ataluren, does not protect mRNAs from NMD. It was reasoned that if there were more mutated mRNA present, these PTC read-through drugs might be more effective. Therefore, the effect of treating K562 cells expressing either wild-type or PTC 39 β globin with a NMDI, the readily available G418, or with both drugs, was examined. There was no effect of any of these treatments on wild-type β globin protein expression (FIG. 5A). G418 or NMDI alone had no effect on PTC39 β globin expression. However, G418 and NMDI resulted in a 3-fold increase in full length β globin expression (FIG. 5A). A similar strategy was tried on N417 cells which contain a PTC mutated p53 gene. Minimal expression of full length p53 in cells treated with G418 was observed, but significantly more was observed in cells treated with both G418 and a NMDI (FIG. 5B). In several other cell lines no change in wild-type p53 was noted. In addition, the combination of both drugs led to a synergistic increase in the p53 targets Bax and PUMA in N417 cells, but not in two cell lines with wild-type p53. Together, these data indicate that NMDIs can increase endogenous mutated mRNAs and, in combination with a PTC-bypass drug, can result in full length protein production.

NMDI can be Achieved with Minimal Cellular Toxicity

NMD inhibition results in the upregulation of mutated and alternatively spliced mRNAs (Gardner "Nonsense-Mediated RNA Decay Regulation by Cellular Stress: Implications for Tumorigenesis," *Mol. Cancer Res.* 8:295-308 (2010), which is hereby incorporated by reference in its entirety) Inhibition of NMD can also result in the accumulation of endogenously non-mutated mRNAs that have been demonstrated to be NMD targets (Gardner, "Hypoxic Inhibition of Nonsense-Mediated RNA Decay Regulates Gene Expression and the Integrated Stress Response," *Mol. Cell Biol.* 28:3729-3741 (2008); Mendell et al., "Nonsense Surveillance Regulates Expression of Diverse Classes of Mammalian Transcripts and Mutes Genomic Noise," *Nat. Genet.* 36:1073-1078 (2004); and Wang et al., "Inhibition of Nonsense-Mediated RNA Decay by the Tumor Microenvironment Promotes Tumorigenesis," *Mol. Cell Biol.* 31:3670-3680 (2011), which are hereby incorporated by reference in their entirety). Thus, NMD inhibition might be predicted to widespread biological effects. Despite the potential toxicity of NMD inhibition, in mice the complete inhibition of NMD by Upf2 depletion in hematopoietic cells results only in diminished hematopoietic progenitor cells with almost no effect on differentiated hematopoietic cells (Weischenfeldt et al., "NMD is Essential for Hematopoietic Stem and Progenitor Cells and for Eliminating By-Products of Programmed DNA Rearrangements," *Genes Dev.* 22:1381-1396 (2008), which is hereby incorporated by reference in its entirety). Similarly, widespread constitutive expression of a dominant negative Upf1 affects only the differentiating thymus (Frischmeyer-Guerrerio et al., "Perturbation of Thymocyte Development in Nonsense-Mediated Decay (NMD)-Deficient Mice," *Proc. Natl. Acad. Sci. U.S.A.* 108:10638-10643 (2011), which is hereby incorporated by reference in its entirety). It has been shown that the genetic depletion of Upf1 or Upf2 effectively inhibit NMD and do not have an effect on cellular proliferation (Wang et al., "Inhibition of Nonsense-Mediated RNA Decay by the Tumor Microenvironment Promotes Tumorigenesis," *Mol. Cell Biol.* 31:3670-3680 (2011), which is hereby incorporated by reference in its entirety). And although it has been shown that the inhibition of NMD by stresses generated by the tumor microenvironment is necessary for tumorigenesis, it has also been shown that the further inhibition of NMD does not augment tumorigenesis (Wang et al., "Inhibition of Nonsense-Mediated RNA Decay by the Tumor Microenvironment Promotes Tumorigenesis," *Mol. Cell Biol.* 31:3670-3680 (2011), which is hereby incorporated by reference in its entirety). To determine the cellular toxicity of select NMDIs, apoptosis in Hela and U2OS cells treated with 50 μM of three effective NMDIs was assessed. Minimal toxicity over 72 hours was observed, in contrast to 12 hours of treatment with emetine which blocks NMD by inhibiting translation (FIG. 7). Although a wide range of concentrations and cell lines have not yet been tested, these data suggest that NMDIs are not necessarily unduly toxic.

The Restoration of Full-Length p53 with NMD Inhibition and a "Read-Through" Drug Leads to Cell Death in Cells with a PTC Mutated p53

Figure 8:
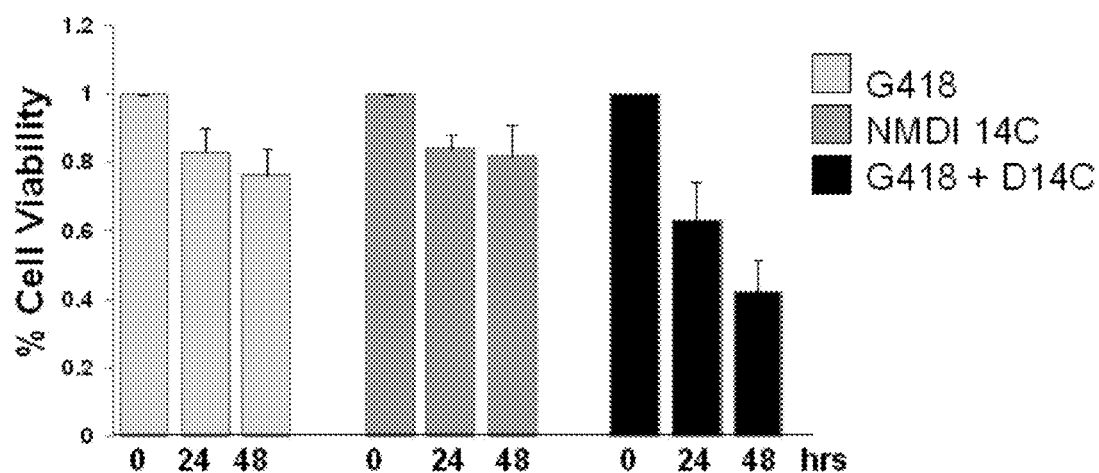
FIG. 8 is a graph showing that restoration of full length p53 leads to cell death. N417 cells with PTC mutated p53 were treated with G418, NMDI14C, or both for up to 48 hrs, and viability was assessed.

The frequently mutated p53 gene is a tumor suppressor which can induce both cell cycle arrest as well as apoptosis. The re-establishment of p53 in cancer cells, with or without chemo/radiation, has been a therapeutic strategy pursued in a wide variety of cancer for almost two decades, but this approach has been hampered by problems in delivery of wild-type p53 (Fujiwara et al., "Induction of Chemosensitivity in Human Lung Cancer Cells In Vivo by Adenovirus-Mediated Transfer of the Wild-Type P53 Gene," *Cancer Res.* 54:2287-2291 (1994) and Gabrilovich, "INGN 201 (Advexin): Adenoviral P53 Gene Therapy for Cancer," *Expert Opin. Biol. Ther.* 6:823-832 (2006), which are hereby incorporated by reference in their entirety). Although NMDIs are relatively non-toxic, it was hypothesized that the combination of NMDI with a "read through" drug would be toxic to cells with a PTC mutated p53. Cells were treated with a combination of read through drug and NMDI that have been demonstrated to restore full length p53 expression (FIGS. 6A-B). A synergistic cell death was noted only with the combination of drugs that led to full length p53 expression (FIG. 8). No such death was seen when G418 and NMDI was used on cells with wild-type p53.

The Combination of NMD Inhibition and NMD Inhibition Leads to Cell Death

The inhibition of NMD is expected to result in the stabilization of mutated and alternatively spliced mRNAs, some of which may be translated into protein. Indeed, it has been observed that the inhibition of NMD, either by depletion of Upf1/Rent1, Upf2/Rent2, of by hypoxia, results in alternatively spliced mRNAs. It was hypothesized that autophagy could play a role. Autophagy is an adaptive process in which damaged organelles and misfolded proteins are sequestered and degraded within cytoplasmic vesicles to allow cells to adapt to stress. Although published data suggest that NMD inhibition augments the ER stress response and promotes tumor growth, it was hypothesized that when autophagy is inhibited, NMD inhibition is no longer protective, but is detrimental. Specifically, it was reasoned that if the induction of autophagy in response to NMD inhibition is a protective mechanism, this autophagic response may be necessary for cell survival.

Figure 9:
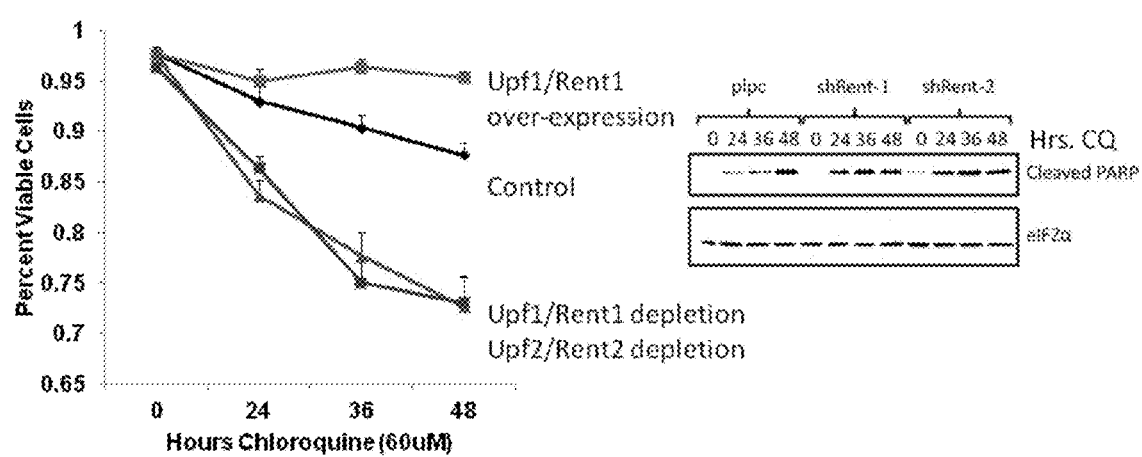
FIG. 9 shows that the combination of autophagy inhibition and NMD inhibition leads to synergistic cell death. HCT116 cells, either control or with Upf1 or Upf2 manipulated, were treated with chlroloquiend for up to 48 hours and cell viability was determined. On the right panel the cell protein was harvested and cleaved PARP, consistent with apoptosis.

Chorloquine, a clinically available and relatively non-toxic anti malarial, is well documented to block autophagy and in fact is currently undergoing trials in humans as an anti-cancer agent. NMD was either inhibited in colon cancer cell lines (HCT116) with Upf1/Rent1 or Upf2/Rent2 depletion, or hyperactivated NMD by over-expressing Upf1/Rent1, and viability with trypan blue was assessed after treatment with choroquine. A modest decrease in cell viability and increase in apoptosis (as noted by PARP cleavage) was noted when control cells were treated with chloqoquine (FIG. 9). Viability was decreased, and apoptosis increased, when NMD inhibited cells were treated with choloroquine. This proof of concept experiment suggests that the simultaneous pharmacological inhibition of NMD and autophagy may be a viable therapeutic strategy to treat cancer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A pharmaceutical composition comprising:
a compound of the formula (I):

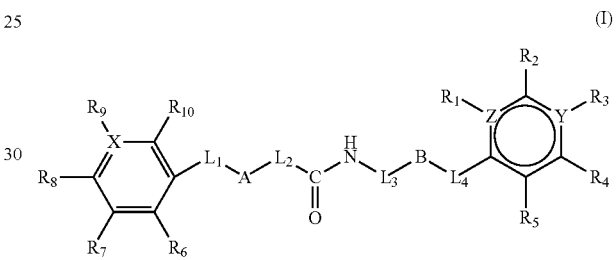

a stereoisomer, pharmaceutically acceptable salt, oxide, solvate, or ester thereof, wherein A is selected from the group consisting of:
(1) absent;
(2) —O—;
(3) —CR$_{11}$=CH—;
(4) —S—;
(5) —CHR$_{12}$NH—;
(6) —NR$_{13}$—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
wherein the substituents of A are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;

B is selected from the group consisting of:
(1) absent;
(2) —O—;
(3) —CR$_{14}$=CH—;
(4) —NH—C(O)—;
(5) —C(S)—NH—;
(6) —N=CH—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
wherein the substituents of B are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;

L₁ to L₄ are independently selected from the group consisting of:
  (1) absent;
  (2) —S$_{0-1}$—C$_{1-6}$ alkylene —S$_{0-1}$—;
  (3) —S$_{0-1}$—C$_{2-4}$ alkenylene —S$_{0-1}$—;
  (4) —S$_{0-1}$—C$_{2-4}$ alkynylene —S$_{0-1}$—; and
  (5) —C(S)—NH—; and
  (6) —NH—;
X is C or N;
Z is C, O, or S;
Y is C or absent;
R$_1$ is absent or, if present, is H, C$_{1-6}$ alkyl, C$_{2-6}$ alkenyl, C$_{2-6}$ alkynyl, OR$_{16}$, C(O)NR$_{17}$R$_{18}$, NR$_{19}$C(O)R$_{20}$;
R$_2$ is H, C$_{1-6}$ alkyl, C$_{2-6}$ alkenyl, C$_{2-6}$ alkynyl, OR$_{16}$, NO$_2$, C(O)N$_{17}$R$_{18}$, NR$_{19}$C(O)R$_{20}$, heterocyclyl or heteroaryl containing 1-5 heteroatoms selected from the group consisting of nitrogen, sulfur, and oxygen;
R$_3$ is H, C$_{1-6}$ alkyl, C$_{2-6}$ alkenyl, C$_{2-6}$ alkynyl, halogen, OR$_{16}$, C(O)NR$_{17}$R$_{18}$, C(O)OR$_{16}$, NR$_{19}$C(O)R$_{20}$;
R$_4$ is H, C$_{1-6}$ alkyl, C$_{2-6}$ alkenyl, C$_{2-6}$ alkynyl, OR$_{16}$, C(O)OR$_{16}$, C(O)NR$_{17}$R$_{18}$, NR$_{19}$C(O)R$_{16}$, heteroaryl containing 1-5 heteroatoms selected from the group consisting of nitrogen, sulfur, and oxygen;
R$_5$ is H, C$_{1-6}$ alkyl, C$_{2-6}$ alkenyl, C$_{2-6}$ alkynyl, halogen, OR$_{16}$, C(O)OR$_{16}$;
R$_6$ is H, C$_{1-6}$ alkyl, C$_{2-6}$ alkenyl, C$_{2-6}$ alkynyl, halogen, OR$_{16}$, NR$_{17}$R$_{18}$, heteroaryl or heterocyclyl containing 1-5 heteroatoms selected from the group consisting of nitrogen, sulfur, and oxygen, N=NR$_{15}$;
R$_7$ is H, C$_{1-6}$ alkyl, C$_{2-6}$ alkenyl, C$_{2-6}$ alkynyl, halogen, OR$_{16}$, NO$_2$, NR$_{19}$C(O)R$_{20}$, S(O)$_2$NR$_{17}$R$_{18}$;
R$_8$ is H, C$_{1-6}$ alkyl, C$_{2-6}$ alkenyl, C$_{2-6}$ alkynyl, halogen, OR$_{16}$, NR$_{19}$C(O)R$_{20}$;
R$_9$ is H, C$_{1-6}$ alkyl, C$_{2-6}$ alkenyl, C$_{2-6}$ alkynyl, halogen, NO$_2$, OR$_{16}$, S(O)$_2$NR$_{21}$R$_{22}$;
R$_{10}$ is H, C$_{1-6}$ alkyl, C$_{2-6}$ alkenyl, C$_{2-6}$ alkynyl, halogen, NR$_{17}$R$_{18}$, OR$_{16}$;
R$_1$ to R$_{10}$ are each optionally substituted 1 to 3 times with substituents selected from the group consisting of halogen, —OH, —OR$_{21}$, —C(O)R$_{21}$, —C(O)OR$_{21}$, C(O)NR$_{21}$R$_{22}$, —NHR$_{21}$, —NR$_{21}$R$_{22}$, —SR$_{21}$, —S(O)R$_{21}$, —S(O)$_2$R$_{21}$, NH$_2$, CN, NO$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;
R$_{11}$ is H, C$_{1-6}$ alkyl, C$_{2-6}$ alkenyl, C$_{3-6}$ alkynyl, NR$_{19}$C(O)R$_{20}$;
R$_{12}$ is H, C$_{1-6}$ alkyl, C$_{2-6}$ alkenyl, C$_{3-6}$ alkynyl, C(O)OR$_{16}$;
R$_{13}$ is NHNH;
R$_{14}$ is C(O)OR$_{21}$;
R$_{10}$ and R$_{12}$ can combine to form a —NH—C(O)— group;
R$_{13}$ and R$_{15}$ can combine to form a —N—N=N— group;
R$_{15}$ to R$_{22}$ are independently H, C$_{1-6}$ alkyl, C$_{2-6}$ alkenyl, C$_{2-6}$ alkynyl, C$_{3-6}$ cycloalkyl, C$_{4-7}$ cycloalkylalky, C$_{1-6}$ alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each R$_{15}$ to R$_{22}$ optionally substituted from 1-3 times with substituents selected from the group consisting of halogen, oxy, OH, CN, NO$_2$, —C(O), NH$_2$, H, C$_{1-6}$ alkyl, C$_{2-6}$ alkenyl, C$_{2-6}$ alkynyl, C$_{3-6}$ cycloalkyl, C$_{4-7}$ cycloalkylalkyl, O-aryl substituted with C$_{1-6}$ alkyl, C(O)NHCH$_2$-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—C$_{1-6}$ alkyl, and a monocyclic aryl;

R$_{21}$ and R$_{22}$ can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, NO$_2$, NH$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, a monocyclic aryl, and monocyclic heteroaryl; and
a pharmaceutically acceptable carrier.

2. The pharmaceutical composition of claim 1, wherein A is a bond, —O+, a C$_{2-6}$ alkenylene with a —CR$_{11}$=CH— moiety, —S—CH$_2$—, —CH$_2$CHR$_{12}$NH—, —CH$_2$NR$_{13}$—,

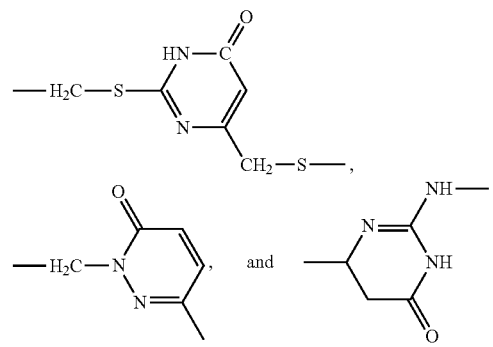

3. The pharmaceutical composition of claim 1, wherein B is a bond, a C$_{2-6}$ alkenylene with a —CR$_{14}$=CH— moiety, —NH—C(O)—, —C(S)—NH—C(CH$_3$)—, —N=CH—,

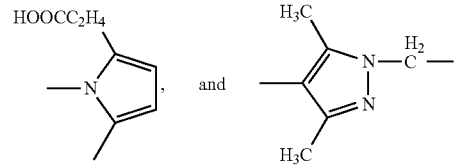

4. The pharmaceutical composition of claim 1, wherein A, B, and L$_1$-L$_4$ are absent.

5. The pharmaceutical composition of claim 1, wherein X is C.

6. The pharmaceutical composition of claim 5, wherein Z is C and Y is C.

7. The pharmaceutical composition of claim 1, wherein X is N.

8. The pharmaceutical composition of claim 1, wherein at least one of R$_1$-R$_{10}$ is independently methyl, halogen, methoxy, or NO$_2$.

9. The pharmaceutical composition of claim 1, wherein the compound is selected from the group consisting of

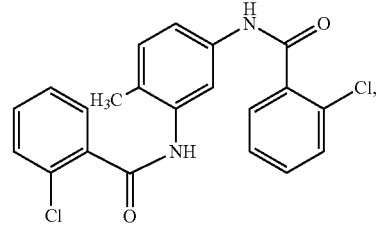

-continued
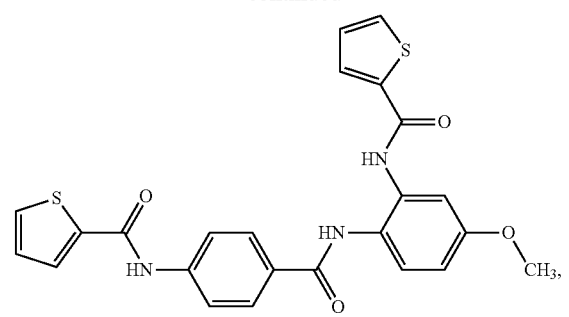
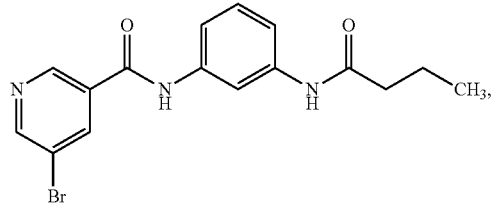
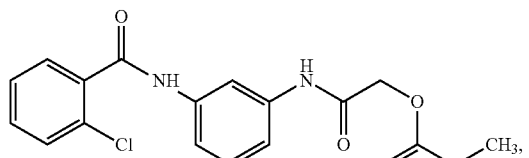
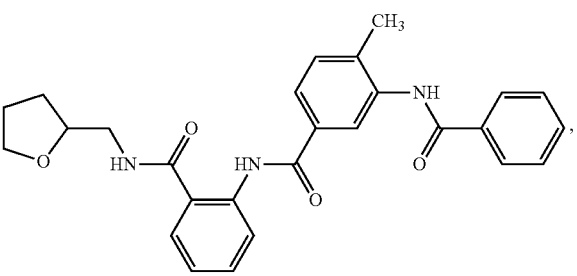
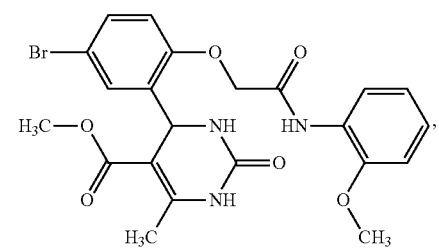
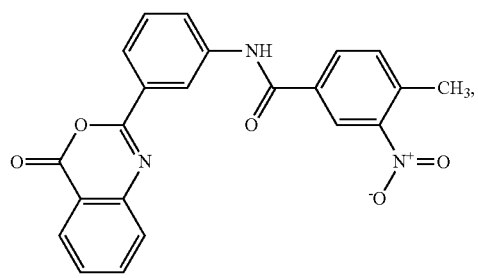
-continued
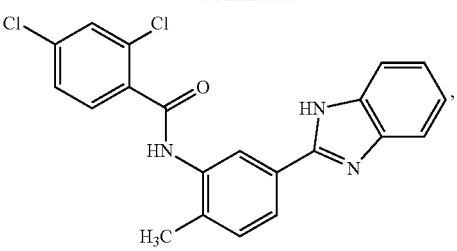
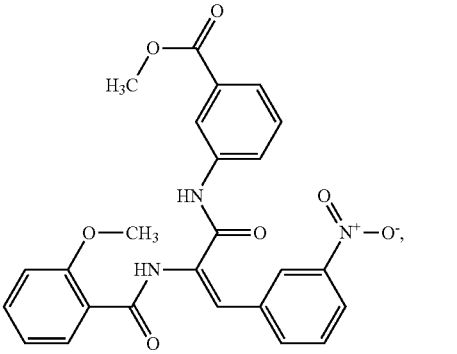
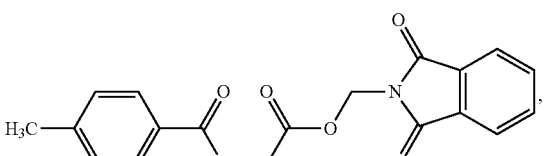
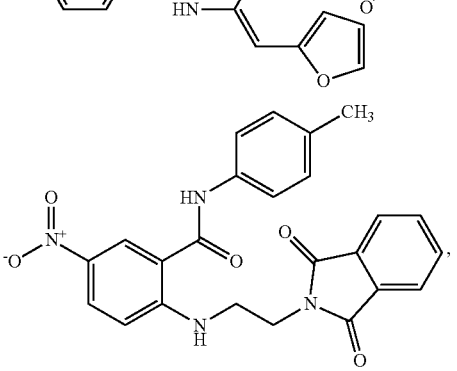
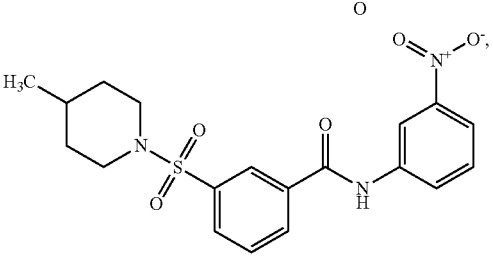
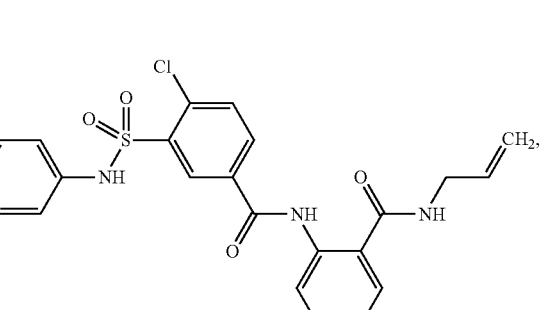

49
-continued
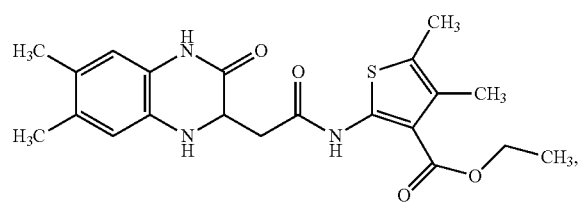
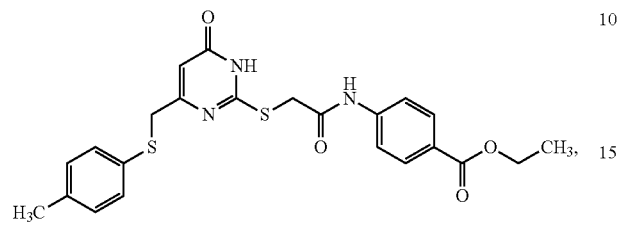
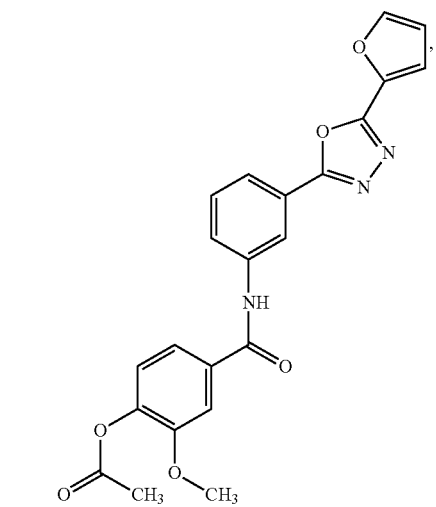
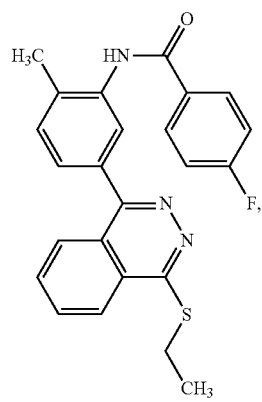
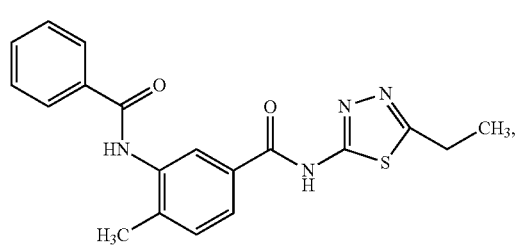
50
-continued
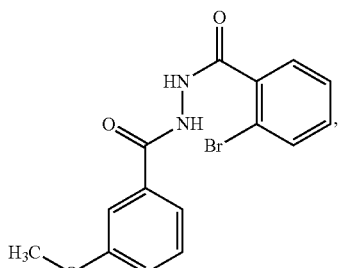
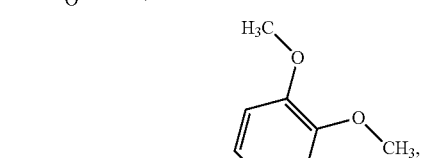
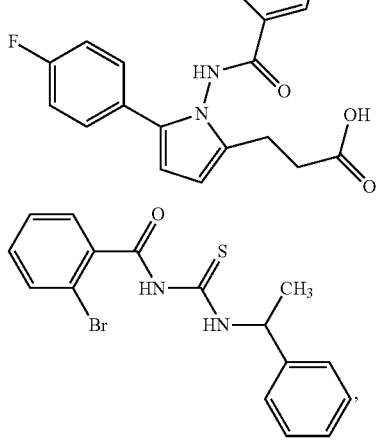
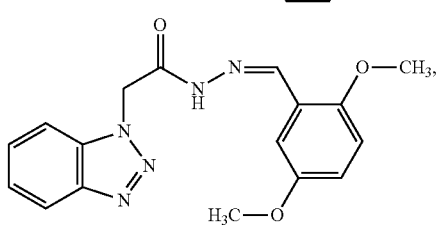
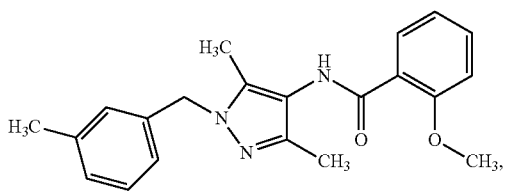
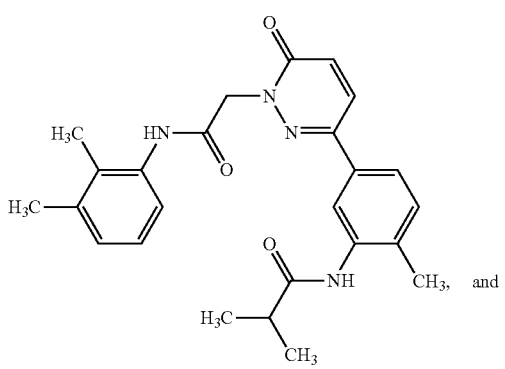
and

51

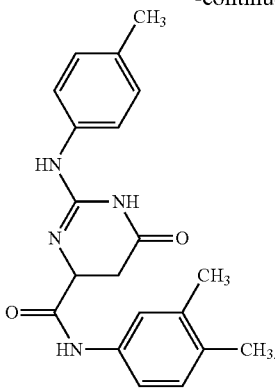

-continued

10. A pharmaceutical composition comprising:
a compound of the formula:

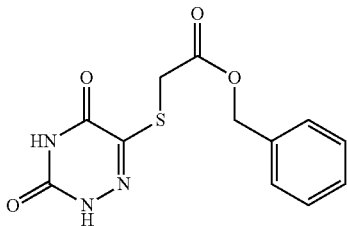 [SMILES: O=C(CSc1n[nH]c(=O)[nH]c1=O)OCc1ccccc1]

a stereoisomer, pharmaceutically acceptable salt, oxide, solvate, or ester thereof and
a pharmaceutically acceptable carrier.

11. A method of treating a genetic disease caused by premature termination codons, or other conditions that render messenger ribonucleic acid (mRNA) susceptible to nonsense mediated RNA decay, in a subject, said method comprising:
selecting a subject with a genetic disease caused by premature termination codons, or other conditions that render messenger ribonucleic acid (mRNA) susceptible to nonsense mediated RNA decay and
administering to the selected subject a compound of the formula

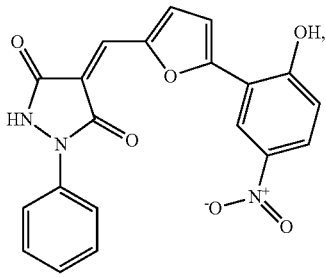

the compound of the formula

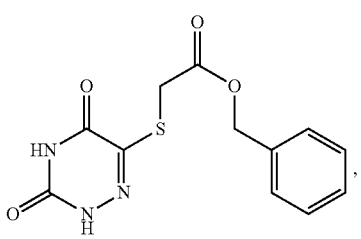

52 or the compound of formula (I):

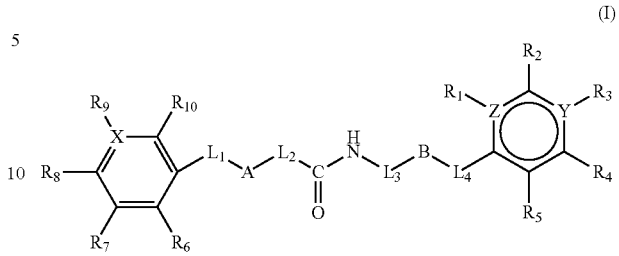

(I)

a stereoisomer, pharmaceutically acceptable salt, oxide, solvate, or ester thereof, wherein
A is selected from the group consisting of:
(1) absent;
(2) —O—;
(3) —$CR_{11}$=CH—;
(4) —S—;
(5) —$CHR_{12}NH$—;
(6) —$NR_{13}$—;
(7) substituted or unsubstituted $C_{3-8}$ cycloalkylene;
(8) substituted or unsubstituted arylene;
(9) substituted or unsubstituted heterocyclylene; and
(10) substituted or unsubstituted heteroarylene
wherein the substituents of A are selected from the group consisting of halogen, OH, CN, $NO_2$, C(O), $NH_2$, H, $C_{1-6}$ alkyl, $C_{1-6}$ alkyl substituted with a —COOH, $C_{2-6}$ alkenyl, $C_{2-6}$ alkynyl, $C_{4-7}$ cycloalkylalkyl, and monocyclic aryl;
B is selected from the group consisting of:
(1) absent;
(2) —O—;
(3) —$CR_{14}$=CH—;
(4) —NH—C(O)—;
(5) —C(S)—NH—;
(6) —N=CH—;
(7) substituted or unsubstituted $C_{3-8}$ cycloalkylene;
(8) substituted or unsubstituted arylene;
(9) substituted or unsubstituted heterocyclylene; and
(10) substituted or unsubstituted heteroarylene
wherein the substituents of B are selected from the group consisting of halogen, OH, CN, $NO_2$, C(O), $NH_2$, H, $C_{1-6}$ alkyl, $C_{1-6}$ alkyl substituted with a —COOH, $C_{2-6}$ alkenyl, $C_{2-6}$ alkynyl, $C_{4-7}$ cycloalkylalkyl, and monocyclic aryl;
$L_1$ to $L_4$ are independently selected from the group consisting of:
(1) absent;
(2) —$S_{0-1}$—$C_{1-6}$ alkylene —$S_{0-1}$—;
(3) —$S_{0-1}$—$C_{2-4}$ alkenylene —$S_{0-1}$—;
(4) —$S_{0-1}$—$C_{2-4}$ alkynylene —$S_{0-1}$—;
(5) —(S)—NH—; and
(6) —NH—;
X is C or N;
Z is C, O, or S;
Y is C or absent;
$R_1$ is absent or, if present, is H, $C_{1-6}$ alkyl, $C_{2-6}$ alkenyl, $C_{2-6}$ alkynyl, $OR_{16}$, $C(O)NR_{17}R_{18}$, $NR_{19}C(O)R_{20}$;
$R_2$ is H, $C_{1-6}$ alkyl, $C_{2-6}$ alkenyl, $C_{2-6}$ alkynyl, $OR_{16}$, $NO_2$, $C(O)N_{17}R_{18}$, $NR_{19}C(O)R_{20}$, heterocycyl or heteroaryl containing 1-5 heteroatoms selected from the group consisting of nitrogen, sulfur, and oxygen;
$R_3$ is H, $C_{1-6}$ alkyl, $C_{2-6}$ alkenyl, $C_{2-6}$ alkynyl, halogen, $OR_{16}$, $C(O)NR_{17}R_{18}$, $C(O)OR_{16}$, $NR_{19}C(O)R_{20}$;
$R_4$ is H, $C_{1-6}$ alkyl, $C_{2-6}$ alkenyl, $C_{2-6}$ alkynyl, $OR_{16}$, $C(O)OR_{16}$, $C(O)NR_{17}R_{18}$, $NR_{19}C(O)R_{16}$, heteroaryl containing 1-5 heteroatoms selected from the group consisting of nitrogen, sulfur, and oxygen;

$R_5$ is H, $C_{1-6}$ alkyl, $C_{2-6}$ alkenyl, $C_{2-6}$ alkynyl, halogen, $OR_{16}$, $C(O)OR_{16}$;

$R_6$ is H, $C_{1-6}$ alkyl, $C_{2-6}$ alkenyl, $C_{2-6}$ alkynyl, halogen, $OR_{16}$, $NR_{17}R_{18}$, heteroaryl or heterocyclyl containing 1-5 heteroatoms selected from the group consisting of nitrogen, sulfur, and oxygen, $N=NR_{15}$;

$R_7$ is H, $C_{1-6}$ alkyl, $C_{2-6}$ alkenyl, $C_{2-6}$ alkynyl, halogen, $OR_{16}$, $NO_2$, $NR_{19}C(O)R_{20}$, $S(O)_2NR_{17}R_{18}$;

$R_8$ is H, $C_{1-6}$ alkyl, $C_{2-6}$ alkenyl, $C_{2-6}$ alkynyl, halogen, $OR_{16}$, $NR_{19}C(O)R_{20}$;

$R_9$ is H, $C_{1-6}$ alkyl, $C_{2-6}$ alkenyl, $C_{2-6}$ alkynyl, halogen, $NO_2$, $OR_{16}$, $S(O)_2NR_{21}R_{22}$;

$R_{10}$ is H, $C_{1-6}$ alkyl, $C_{2-6}$ alkenyl, $C_{2-6}$ alkynyl, halogen, $NR_{17}R_{18}$, $OR_{16}$;

$R_1$ to $R_{10}$ are each optionally substituted 1 to 3 times with substituents selected from the group consisting of halogen, —OH, —$OR_{21}$, —$C(O)R_{21}$, —$C(O)OR_{21}$, $C(O)NR_{21}R_{22}$, —$NHR_{21}$, —$NR_{21}R_{22}$, —$SR_{21}$, —$S(O)R_{21}$, —$S(O)_2R_{21}$, $NH_2$, CN, $NO_2$, $C_{1-6}$ alkyl, $C_{2-6}$ alkenyl, $C_{2-6}$ alkynyl, $C_{3-6}$ cycloalkyl, $C_{4-7}$ cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;

$R_{11}$ is H, $C_{1-6}$ alkyl, $C_{2-6}$ alkenyl, $C_{3-6}$ alkynyl, $NR_{19}C(O)R_{20}$;
$R_{12}$ is H, $C_{1-6}$ alkyl, $C_{2-6}$ alkenyl, $C_{3-6}$ alkynyl, $C(O)OR_{16}$;
$R_{13}$ is NHNH;
$R_{14}$ is $C(O)OR_{21}$;
$R_{10}$ and $R_{12}$ can combine to form a —NH—C(O)— group;
$R_{13}$ and $R_{15}$ can combine to form a —N—N=N— group;
$R_{15}$ to $R_{22}$ are independently H, $C_{1-6}$ alkyl, $C_{2-6}$ alkenyl, $C_{2-6}$ alkynyl, $C_{3-6}$ cycloalkyl, $C_{4-7}$ cycloalkylalky, $C_{1-6}$ alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each $R_{15}$ to $R_{22}$ optionally substituted from 1-3 times with substituents selected from the group consisting of halogen, oxy, OH, CN, $NO_2$, —C(O), $NH_2$, H, $C_{1-6}$ alkyl, $C_{2-6}$ alkenyl, $C_{2-6}$ alkynyl, $C_{3-6}$ cycloalkyl, $C_{4-7}$ cycloalkylalkyl, O-aryl substituted with $C_{1-6}$ alkyl, $C(O)NHCH_2$-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—$C_{1-6}$ alkyl, and a monocyclic aryl;

$R_{21}$ and $R_{22}$ can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, $NO_2$, $NH_2$, $C_{1-6}$ alkyl, $C_{2-6}$ alkenyl, $C_{2-6}$ alkynyl, $C_{3-6}$ cycloalkyl, $C_{4-7}$ cycloalkylalkyl, a monocyclic aryl, and monocyclic heteroaryl under conditions effective to treat the genetic disease caused by premature termination codons, or other conditions that render messenger ribonucleic acid (mRNA) susceptible to nonsense mediated RNA decay.

12. The method of claim 11, wherein the genetic disease is selected from the group consisting of thalassemia, muscular dystrophy, cystic fibrosis, polycystic kidney disease, Marfan's disease, Hurler's disease, Ullrich disease, cancer, cancer with APC mutation, WTI mutations, p53 mutation, BRCA 1/2 mutations, and where NMD is to be inhibited to increase immunogenicity.

13. The method of claim 11, wherein A is a bond, —O—, a $C_{2-6}$ alkenylene with a —$CR_{11}$=CH— moiety, —S—$CH_2$—, —$CH_2CHR_{12}NH$—, —$CH_2NR_{13}$—,

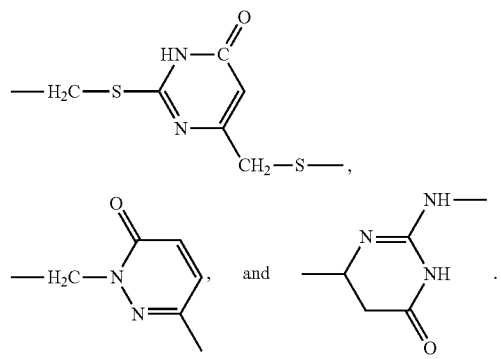

14. The method of claim 11, wherein B is a bond, a $C_{2-6}$ alkenylene with a —$CR_{14}$=CH— moiety, —NH—C(O)—, —C(S)—NH—C(CH$_3$)—, —N=CH—,

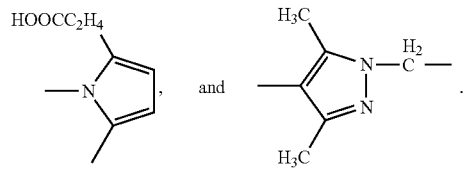

15. The method of claim 11, wherein A, B, and $L_1$-$L_4$ are absent.

16. The method of claim 11, wherein X is C.

17. The method of claim 16, wherein Z is C and Y is C.

18. The method of claim 11, wherein X is N.

19. The method of claim 11, wherein at least one of $R_1$-$R_{10}$ is independently methyl, halogen, methoxy, or $NO_2$.

20. The method of claim 11, wherein the compound is selected from the group consisting of

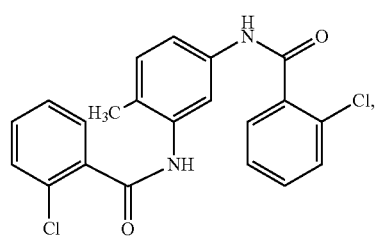

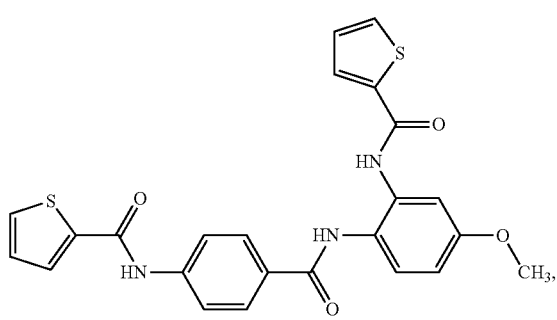

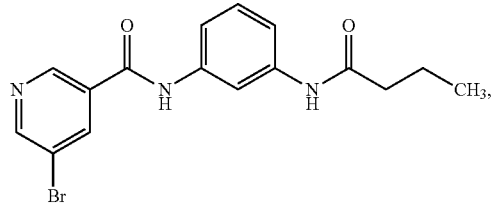
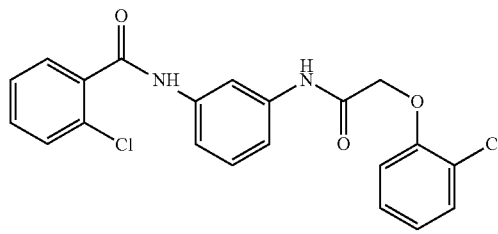
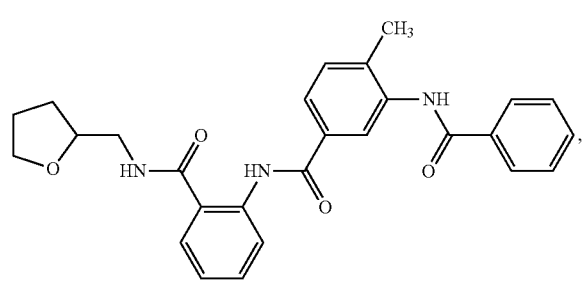
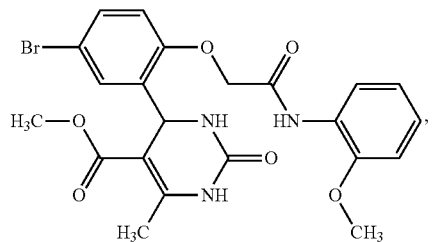
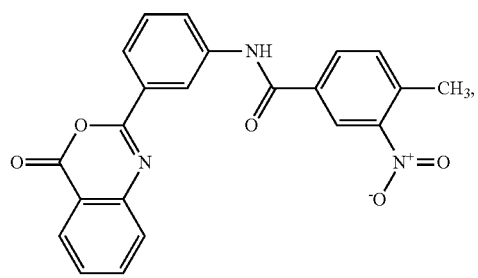
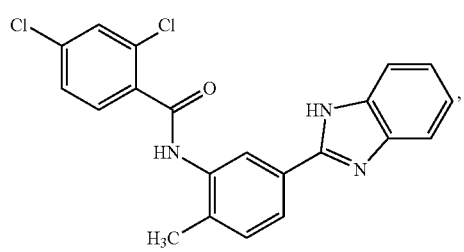
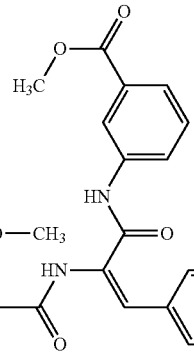
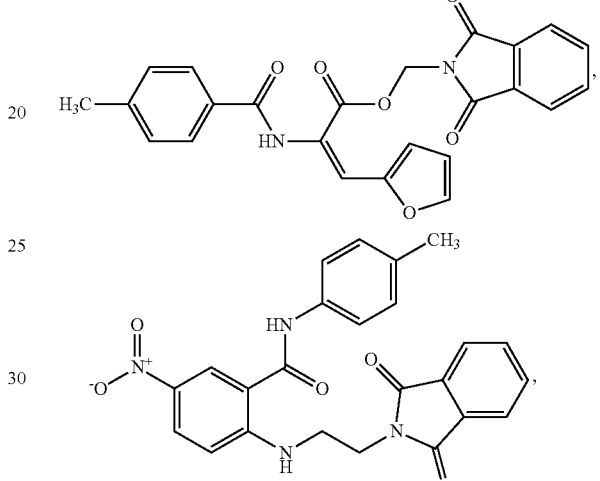
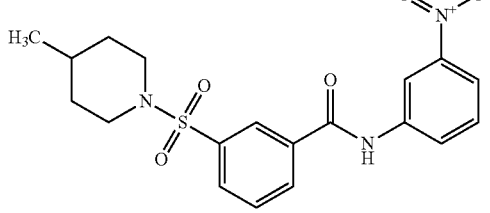
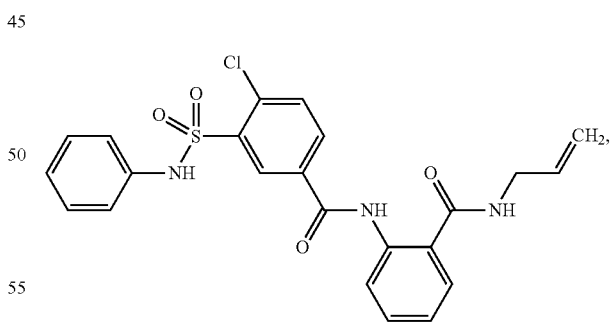
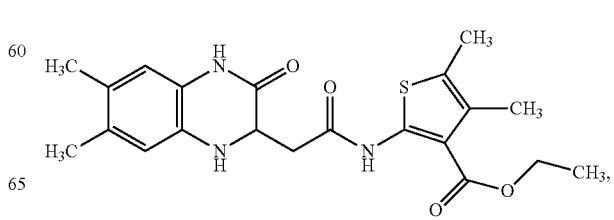

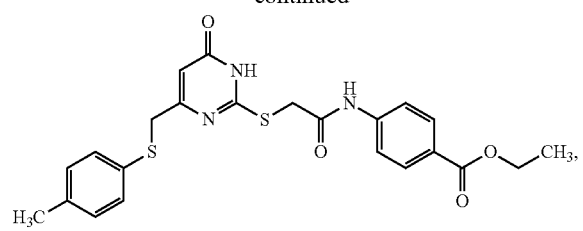
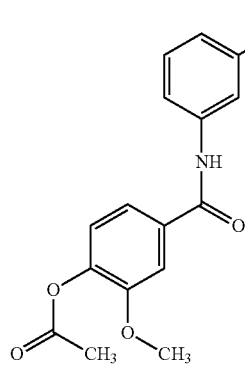
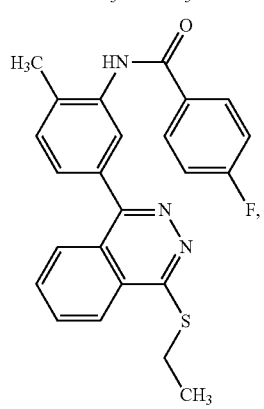
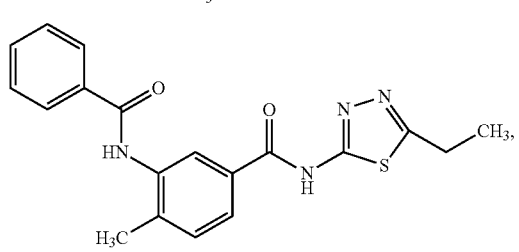
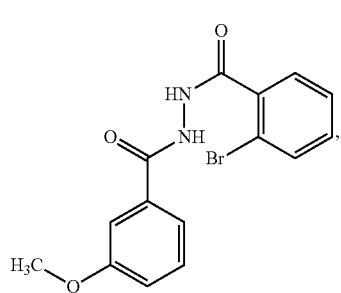
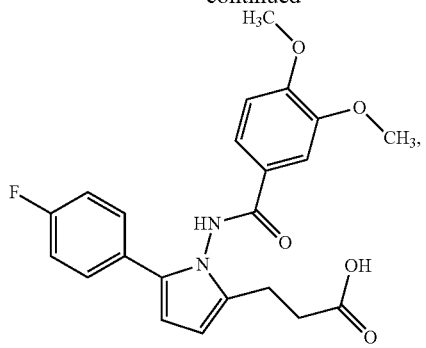
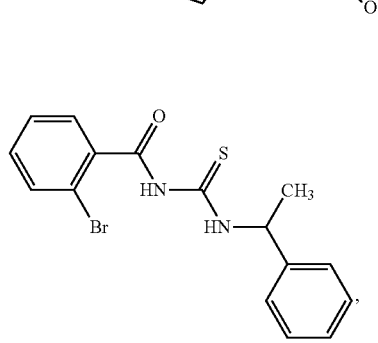
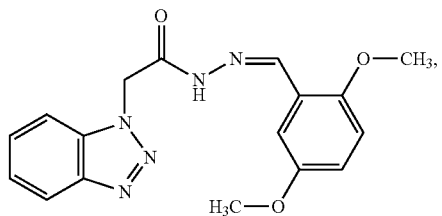
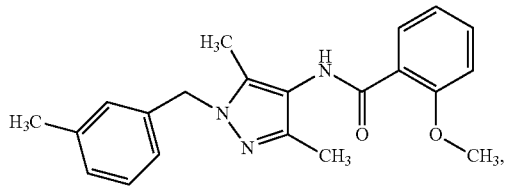
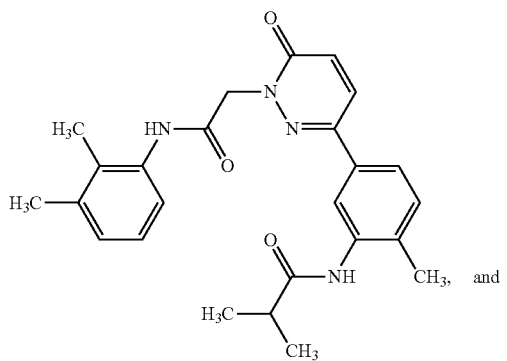

-continued

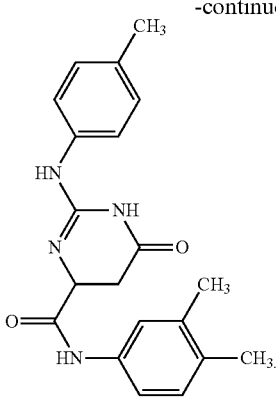

21. The method of claim 11, wherein said administering is carried out in combination with an agent that promotes ribosomal read-through of a premature termination codon to treat the genetic disease or in combination with an agent that inhibits autophagy.

22. A method of inhibiting nonsense mediated RNA decay and induction of autophagy comprising:
administering to cells a compound of the formula:

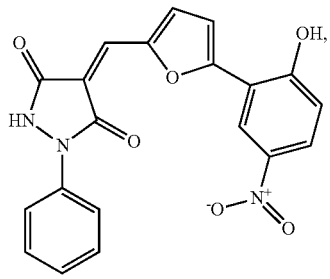

the compound of the formula:

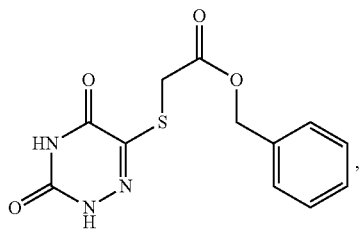 [SMILES: O=C(CSc1n[nH]c(=O)[nH]c1=O)OCc1ccccc1]

or the compound of formula (I):

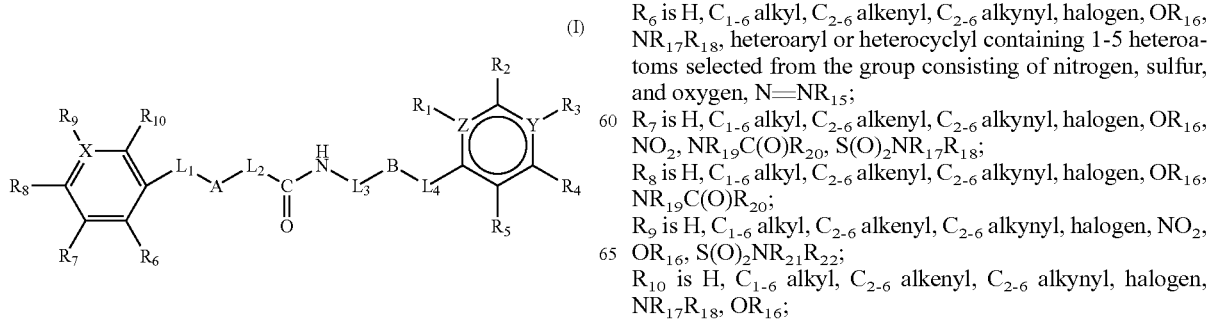

a stereoisomer, pharmaceutically acceptable salt, oxide, solvate, or ester thereof, wherein
A is selected from the group consisting of:
(1) absent;
(2) —O—;
(3) —CR$_{11}$=CH—;
(4) —S—;
(5) —CHR$_{12}$NH—;
(6) —NR$_{13}$—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
wherein the substituents of A are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;
B is selected from the group consisting of:
(1) absent;
(2) —O—;
(3) —CR$_{14}$=CH—;
(4) —NH—C(O)—;
(5) —C(S)—NH—;
(6) —N=CH—;
(7) substituted or unsubstituted C$_{3-8}$ cycloalkylene;
(8) substituted or unsubstituted arylene;
(9) substituted or unsubstituted heterocyclylene; and
(10) substituted or unsubstituted heteroarylene
wherein the substituents of B are selected from the group consisting of halogen, OH, CN, NO$_2$, C(O), NH$_2$, H, C$_{1-6}$ alkyl, C$_{1-6}$ alkyl substituted with a —COOH, C$_{2-6}$ alkenyl, C$_{2-6}$ alkynyl, C$_{4-7}$ cycloalkylalkyl, and monocyclic aryl;
L$_1$ to L$_4$ are independently selected from the group consisting of:
(1) absent;
(2) —S$_{0-1}$—C$_{1-6}$ alkylene —S$_{0-1}$—;
(3) —S$_{0-1}$—C$_{2-4}$ alkenylene —S$_{0-1}$—;
(4) —S$_{0-1}$—C$_{2-4}$ alkynylene —S$_{0-1}$—;
(5) —(S)—NH—; and
(6) —NH—;
X is C or N;
Z is C, O, or S;
Y is C or absent;
R$_1$ is absent or, if present, is H, C$_{1-6}$ alkyl, C$_{2-6}$ alkenyl, C$_{2-6}$ alkynyl, OR$_{16}$, C(O)NR$_{17}$R$_{18}$, NR$_{19}$C(O)R$_{20}$;
R$_2$ is H, C$_{1-6}$ alkyl, C$_{2-6}$ alkenyl, C$_{2-6}$ alkynyl, OR$_{16}$, NO$_2$, C(O)N$_{17}$R$_{18}$, NR$_{19}$C(O)R$_{20}$, heterocycyl or heteroaryl containing 1-5 heteroatoms selected from the group consisting of nitrogen, sulfur, and oxygen;
R$_3$ is H, C$_{1-6}$ alkyl, C$_{2-6}$ alkenyl, C$_{2-6}$ alkynyl, halogen, OR$_{16}$, C(O)NR$_{17}$R$_{18}$, C(O)OR$_{16}$, NR$_{19}$C(O)R$_{20}$;
R$_4$ is H, C$_{1-6}$ alkyl, C$_{2-6}$ alkenyl, C$_{2-6}$ alkynyl, OR$_{16}$, C(O)OR$_{16}$, C(O)NR$_{17}$R$_{18}$, NR$_{19}$C(O)R$_{16}$, heteroaryl containing 1-5 heteroatoms selected from the group consisting of nitrogen, sulfur, and oxygen;
R$_5$ is H, C$_{1-6}$ alkyl, C$_{2-6}$ alkenyl, C$_{2-6}$ alkynyl, halogen, OR$_{16}$, C(O)OR$_{16}$;
R$_6$ is H, C$_{1-6}$ alkyl, C$_{2-6}$ alkenyl, C$_{2-6}$ alkynyl, halogen, OR$_{16}$, NR$_{17}$R$_{18}$, heteroaryl or heterocyclyl containing 1-5 heteroatoms selected from the group consisting of nitrogen, sulfur, and oxygen, N=NR$_{15}$;
R$_7$ is H, C$_{1-6}$ alkyl, C$_{2-6}$ alkenyl, C$_{2-6}$ alkynyl, halogen, OR$_{16}$, NO$_2$, NR$_{19}$C(O)R$_{20}$, S(O)$_2$NR$_{17}$R$_{18}$;
R$_8$ is H, C$_{1-6}$ alkyl, C$_{2-6}$ alkenyl, C$_{2-6}$ alkynyl, halogen, OR$_{16}$, NR$_{19}$C(O)R$_{20}$;
R$_9$ is H, C$_{1-6}$ alkyl, C$_{2-6}$ alkenyl, C$_{2-6}$ alkynyl, halogen, NO$_2$, OR$_{16}$, S(O)$_2$NR$_{21}$R$_{22}$;
R$_{10}$ is H, C$_{1-6}$ alkyl, C$_{2-6}$ alkenyl, C$_{2-6}$ alkynyl, halogen, NR$_{17}$R$_{18}$, OR$_{16}$;

$R_1$ to $R_{10}$ are each optionally substituted 1 to 3 times with substituents selected from the group consisting of halogen, —OH, —OR$_{21}$, —C(O)R$_{21}$, —C(O)OR$_{21}$, C(O)NR$_{21}$R$_{22}$, —NHR$_{21}$, —NR$_{21}$R$_{22}$, —SR$_{21}$, —S(O)R$_{21}$, —S(O)$_2$R$_{21}$, NH$_2$, CN, NO$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, mono- or polycyclic aryl, and mono- or polycyclic heteroaryl containing 1 to 5 heteroatoms selected from the group consisting of nitrogen, sulfur, and oxygen and, optionally, oxy substituted;

$R_{11}$ is H, C$_{1-6}$ alkyl, C$_{2-6}$ alkenyl, C$_{3-6}$ alkynyl, NR$_{19}$C(O)R$_{20}$;
$R_{12}$ is H, C$_{1-6}$ alkyl, C$_{2-6}$ alkenyl, C$_{3-6}$ alkynyl, C(O)OR$_{16}$;
$R_{13}$ is NHNH;
$R_{14}$ is C(O)OR$_{21}$;
$R_{10}$ and $R_{12}$ can combine to form a —NH—C(O)— group;
$R_{13}$ and $R_{15}$ can combine to form a —N—N=N— group;
$R_{15}$ to $R_{22}$ are independently H, C$_{1-6}$ alkyl, C$_{2-6}$ alkenyl, C$_{2-6}$ alkynyl, C$_{3-6}$ cycloalkyl, C$_{4-7}$ cycloalkylalky, C$_{1-6}$ alkoxy, carboxy, a monocyclic or polycyclic aryl, or a monocyclic or polycyclic heterocyclyl or heteroaryl containing 1-5 heteroatoms selected from the group consisting of nitrogen, oxygen, and sulfur, each $R_{15}$ to $R_{22}$ optionally substituted from 1-3 times with substituents selected from the group consisting of halogen, oxy, OH, CN, NO$_2$, —C(O), NH$_2$, H, C$_{1-6}$ alkyl, C$_{2-6}$ alkenyl, C$_{2-6}$ alkynyl, C$_{3-6}$ cycloalkyl, C$_{4-7}$ cycloalkylalkyl, O-aryl substituted with C$_{1-6}$ alkyl, C(O)NHCH$_2$-heterocyclyl with 1-5 oxygen, sulfur, or nitrogen heteroatoms, heteroaryl with 1-5 heteroatoms selected from the group consisting of oxygen, sulfur, or nitrogen heteroatoms, —S—C$_{1-6}$ alkyl, and a monocyclic aryl;

$R_{21}$ and $R_{22}$ can combine to form a 3-7-membered mono- or polycyclic heterocycle or mono- or polycyclic heteroaryl each containing 1-5 heteroatoms selected from the group consisting of nitrogen, sulfur, and oxygen, where the heterocycle or heteroaryl are optionally substituted from 1 to 3 times with substituents selected from the group consisting of halogen, OH, CN, NO$_2$, NH$_2$, C$_{1-6}$ alkyl, C$_{2-6}$ alkenyl, C$_{2-6}$ alkynyl, C$_{3-6}$ cycloalkyl, C$_{4-7}$ cycloalkylalkyl, a monocyclic aryl, and monocyclic heteroaryl under conditions effective to inhibit nonsense mediated RNA decay and induce autophagy.

23. The method of claim 22, wherein the method is carried out in vivo.
24. The method of claim 22, wherein the method is carried out in vitro.
25. The method of claim 22, wherein A is a bond, —O—, a C$_{2-6}$ alkenylene with a —CR$_{11}$=CH— moiety, —S—CH$_2$—, —CH$_2$CHR$_{12}$NH—, —CH$_2$NR$_{13}$—,

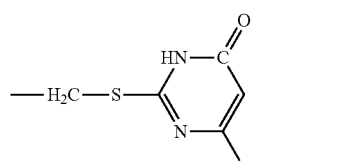

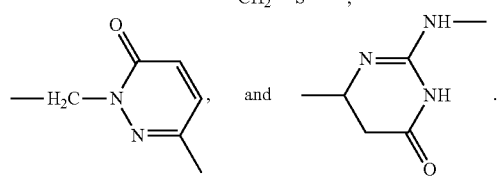

26. The method of claim 22, wherein B is a bond, a C$_{2-6}$ alkenylene with a —CR$_{14}$=CH— moiety, —NH—C(O), —C(S)—NH—C(CH$_3$)—, —N=CH—,

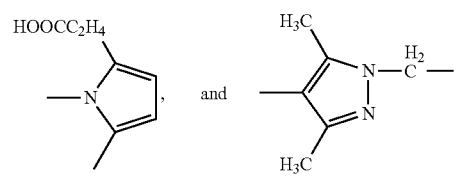

27. The method of claim 22, wherein A, B, and L$_1$-L$_4$ are absent.
28. The method of claim 22, wherein X is C.
29. The method of claim 28, wherein Z is C and Y is C.
30. The method of claim 22, wherein X is N.
31. The method of claim 22, wherein at least one of $R_1$-$R_{10}$ is independently methyl, halogen, methoxy, or NO$_2$.
32. The method of claim 22, wherein the compound is selected from the group consisting of

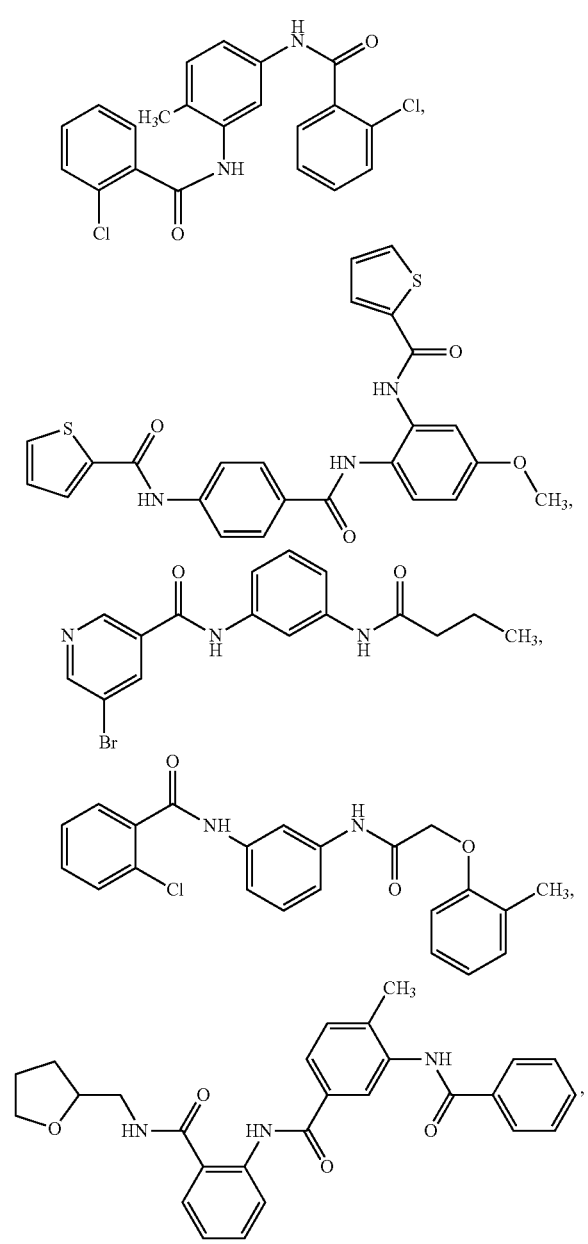

63
-continued
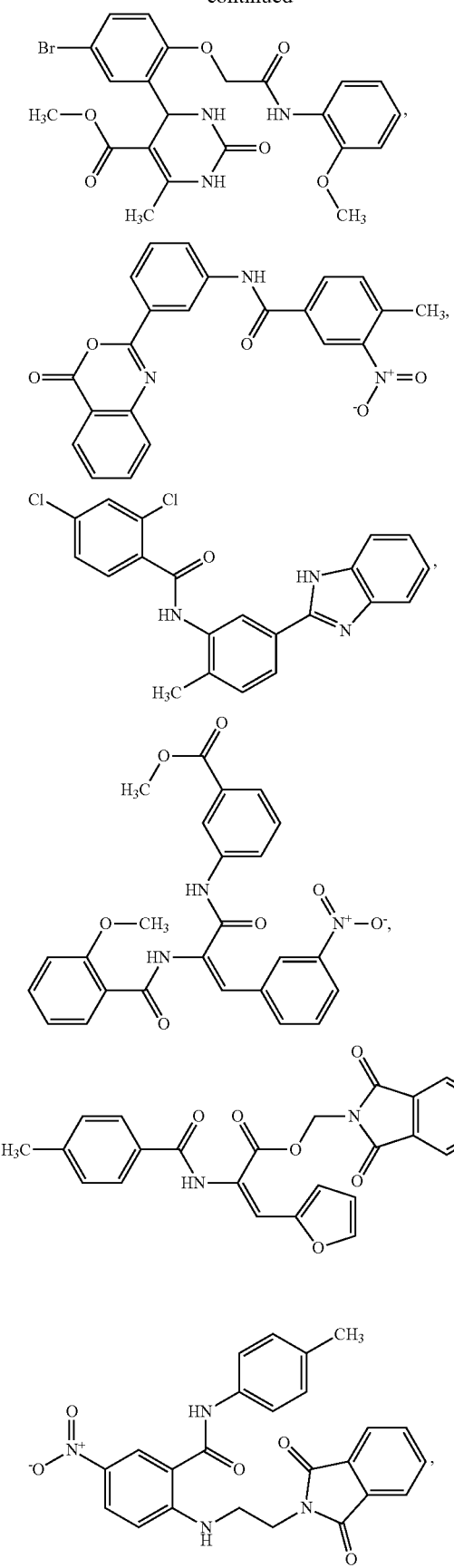
64
-continued
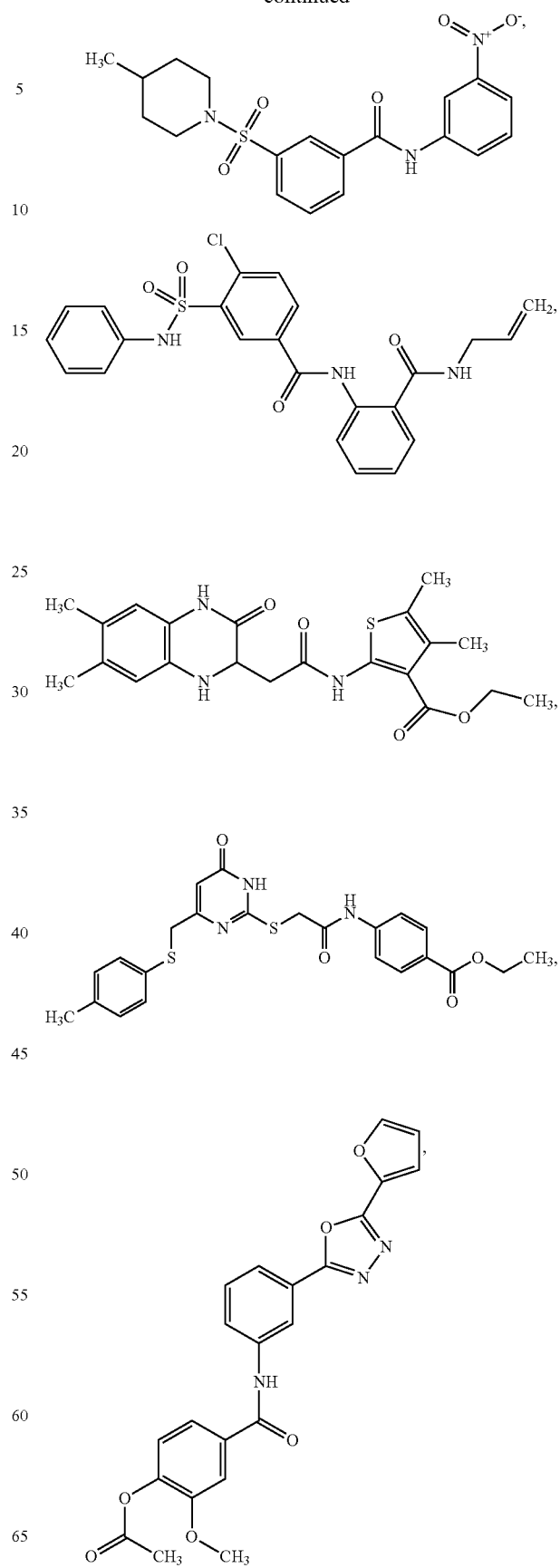

-continued

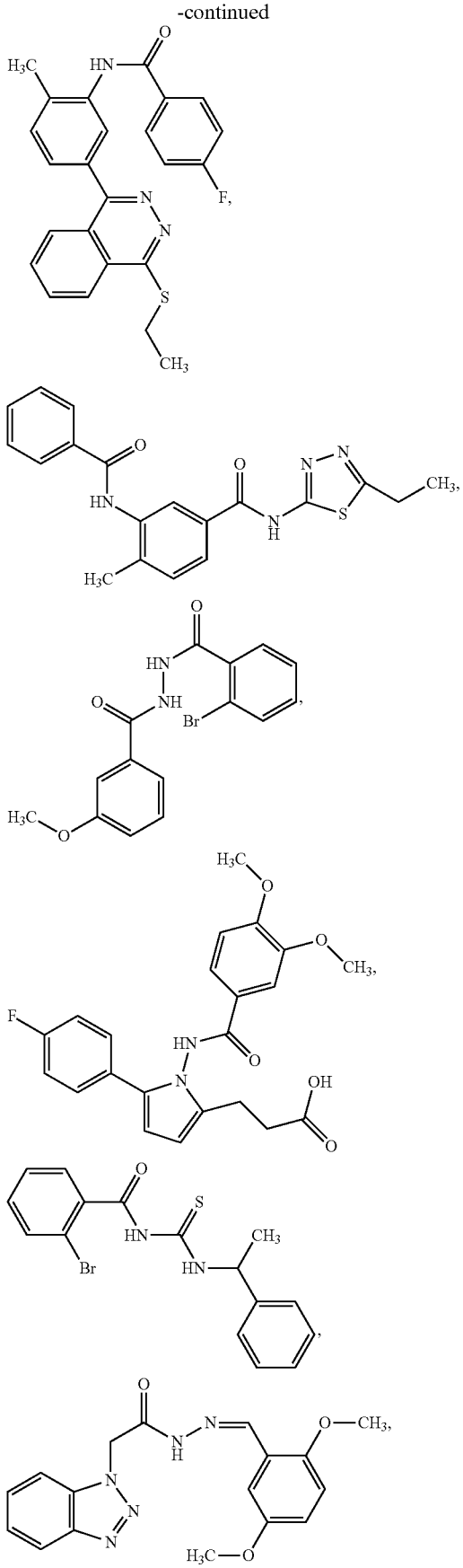

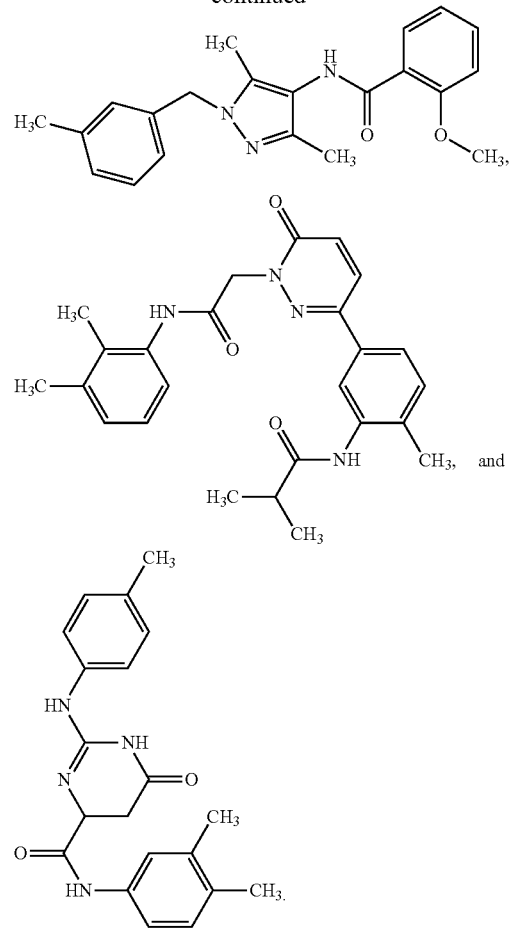

33. The method of claim 22, wherein said administering is carried out in combination with an agent that promotes ribosomal read-through of a premature termination codon to treat the genetic disease or in combination with an agent that inhibits autophagy.

34. A method of identifying inhibitors of nonsense mediated RNA decay, said method comprising:
   providing a model comprising an SMG7-Upf1 complex interface;
   providing one or more candidate compounds;
   evaluating contact between the candidate compounds and the model to determine which of the one or more candidate compounds have an ability to bind to the SMG7-Upf1 interface of the first model; and
   identifying compounds which, based on said evaluating, have the ability to bind to the SMG7-Upf1 interface of the model as compounds potentially useful as inhibitors of nonsense mediated RNA decay.

35. The method according to claim 34 further comprising:
   screening the identified compounds in vitro for their ability to inhibit nonsense mediated RNA decay or their ability to induce autophagy or for their ability to treat genetic disease and
   designating the screened compounds which inhibit nonsense mediated RNA decay or induce autophagy or which treat genetic disease as a useful therapeutic.

36. The method according to claim 34, wherein said evaluating comprises using automated docking algorithms.

37. The method according to claim 34, wherein said evaluating involves analyzing electrostatic complementarity, vander Waals interactions, hydrophilic interactions, hydrophobic interactions, and/or hydrogen bonding between the candidate compounds and the first model.

38. The method according to claim 34 further comprising:
designing de novo compounds based on said identifying.

39. The method according to claim 38, wherein said designing comprises:
linking functional groups or small molecule fragments of the identified compounds to form de novo compounds.

40. A method of inhibiting nonsense mediated RNA decay in a subject comprising:
selecting a subject in need of inhibiting nonsense mediated RNA decay;
providing a compound which binds to SMG7-Upf1 complex interface; and
administering the compound to the selected subject under conditions effective to inhibit nonsense mediated RNA decay in the subject.

41. The method according to claim 40, wherein the administering is carried out in vivo.

42. The method according to claim 40, wherein the said administering is carried out orally, topically, transdermally, parenterally, subcutaneously, intravenously, intramuscularly, intraperitoneally, by intranasal instillation, by intracavitary or intavesical instillation, intraocularly, intraarterially, intralesionally, or by application to mucous membranes.

43. The method according to claim 40, wherein the subject is a mammal.

44. The method according to claim 43, wherein the subject is human.

* * * * *